(12) United States Patent
Selanikio

(10) Patent No.: US 9,241,909 B2
(45) Date of Patent: Jan. 26, 2016

(54) PHARMACEUTICAL COMPOSITIONS AND METHODS FOR VERIFYING DOSING COMPLIANCE

(76) Inventor: Joel David Selanikio, Washington, DC (US)

( * ) Notice: Subject to any disclaimer, the term of this patent is extended or adjusted under 35 U.S.C. 154(b) by 1309 days.

(21) Appl. No.: 13/095,834

(22) Filed: Apr. 27, 2011

(65) Prior Publication Data

US 2011/0264696 A1     Oct. 27, 2011

Related U.S. Application Data

(60) Provisional application No. 61/328,310, filed on Apr. 27, 2010, provisional application No. 61/410,917, filed on Nov. 7, 2010.

(51) Int. Cl.
| | |
|---|---|
| G06F 17/00 | (2006.01) |
| A61K 9/28 | (2006.01) |
| A61J 7/04 | (2006.01) |
| A61K 9/00 | (2006.01) |

(52) U.S. Cl.
CPC ............. *A61K 9/2866* (2013.01); *A61J 7/0481* (2013.01); *A61K 9/0056* (2013.01); *A61K 9/0095* (2013.01); *A61J 2200/30* (2013.01); *A61J 2205/10* (2013.01); *A61J 2205/20* (2013.01)

(58) Field of Classification Search
USPC ................. 235/375, 462.01, 462.09; 705/2, 3
See application file for complete search history.

(56) References Cited

U.S. PATENT DOCUMENTS

| | | | | |
|---|---|---|---|---|
| 2010/0223069 | A1* | 9/2010 | Kim .................................. | 705/2 |
| 2010/0283601 | A1* | 11/2010 | Tai et al. .................. | 340/539.12 |
| 2011/0093279 | A1* | 4/2011 | Levine et al. ..................... | 705/2 |

* cited by examiner

*Primary Examiner* — Ahshik Kim
(74) *Attorney, Agent, or Firm* — William D. Hare; McNeely, Hare & War, LLP

(57) ABSTRACT

A pharmaceutical dosage form is provided that has a distinguishing characteristic and an identifier associated with the dosage form. The distinguishing characteristic is assigned from a limited set of distinguishing characteristics and is determined upon oral administration of the dosage form, or is detected in breath, bodily fluids, or tissues after ingestion, or injection or other non-oral administration. The identifier is associated with the dosage form and with the distinguishing characteristic. The identifier is associated with only one distinguishing characteristic but the distinguishing characteristic may be associated with multiple identifiers. The pharmaceutical dosage form may be used in a method to monitor compliance with a dosage regimen.

19 Claims, 7 Drawing Sheets

100 – Drug Compliance Monitoring System
105 – Drug dispensing entity
110 – drug dosage
115 – drug dosage unique ID
116 – drug dosage distinguishing characteristic
117 – date and time stamp
120 – patient
125 – patient ID
130 – patient data entry means
140 – data transmission over the Internet
150 – server with compliance monitoring software
155 – compliance monitoring software
160 – database on computer-readable memory with tables for patient ID, drug dosage ID and distinguishing characteristic
170 – software-based data analysis capability on computer-readable memory
180 – software-based reporting capability on computer-readable memory
190 – user interface of compliance monitoring system software
195 – clinic or other entity with system containing patient record

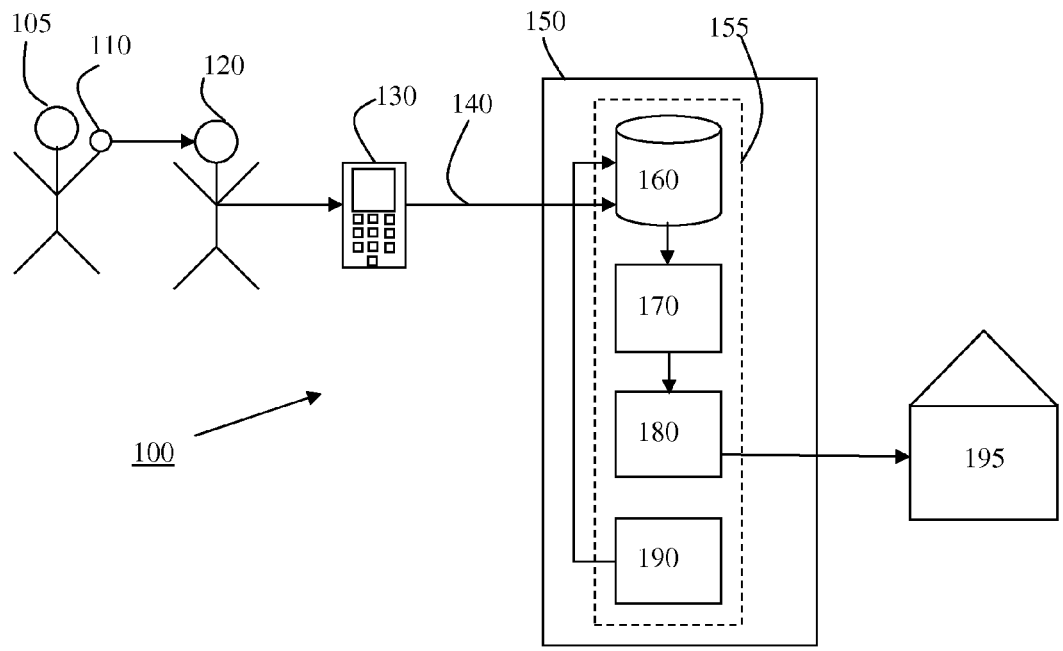

FIG. 1

100 – Drug Compliance Monitoring System
105 – Drug dispensing entity
110 – drug dosage
115 – drug dosage unique ID
116 – drug dosage distinguishing characteristic
117 – date and time stamp
120 – patient
125 – patient ID
130 – patient data entry means
140 – data transmission over the Internet
150 – server with compliance monitoring software
155 – compliance monitoring software
160 – database on computer-readable memory with tables for patient ID, drug dosage ID and distinguishing characteristic
170 – software-based data analysis capability on computer-readable memory
180 – software-based reporting capability on computer-readable memory
190 – user interface of compliance monitoring system software
195 – clinic or other entity with system containing patient record 155 – Drug Compliance Monitoring System software.
160 - Database
170 - Analysis Capability
180 – Alerting and Reporting
190 - User Interface

PHARMACEUTICAL COMPOSITIONS AND METHODS FOR VERIFYING DOSING COMPLIANCE

CROSS-REFERENCE TO RELATED APPLICATIONS

This application is a nonprovisional application claiming priority to U.S. Application No. 61/328,310, filed on Apr. 27, 2010 and U.S. Application No. 61/410,917, filed on Nov. 7, 2010, the contents of which are incorporated herein in their entirety by reference.

TECHNICAL FIELD

The field of the invention generally relates to pharmaceutical dosage forms that have been formulated for use in a system to monitor compliance with a dosing regimen of a pharmaceutical. The invention also includes a method and software system that can use these dosage forms to monitor dosing regimen compliance and/or determine whether the dosage form is a counterfeit or not.

BACKGROUND

The system is designed, in part, to address a problem of significant resources being spent on monitoring patients, or clinical drug study enrollees, in person to ensure they take a drug dosage and take it according to the appropriate dosing regimen. Certain pharmaceuticals, such as antibiotics and treatments for tuberculosis, HIV, and malaria, must be administered according to a strict dosing regimen to ensure that the patient is properly treated, does not skip individual dosings or ceases treatment early. Besides the danger of the condition re-emerging following premature termination of treatment, certain bacterial and viral strains may become treatment resistant if the full treatment course is not followed or is not followed according to the dosage regimen.

Of course, the need to ensure patients take their medication is not limited to treating conditions in which development of a drug resistance organism is a concern. The clinic may be spending extra resources to ensure patient compliance with the dosing regimen solely to ensure that patients recover. Those resources could be better spent on medications if the clinic knows which patients take the medication and which patients do not.

To address these concerns, a significant amount of the public health money spent worldwide is not spent on the medicines themselves but instead is directed to efforts to ensure compliance with the dosing regimen. One of these methods is directly observed therapy (DOT), in which the patient visits the clinic to be administered the medicine under direct observation of the health care provider. Alternatively, the health care provider travels to the patient to directly observe administration of the medicine to the patient. In either situation, there is a waste of resources: either the patient is wasting resources traveling to a clinic on a periodic basis to ensure that someone observes that they are taking the medicine, or a health care provider is wasting resources traveling to the patient to directly observe the patient taking the medicine. For many patients who live in rural areas of developing nations, traveling to a health care provider can be very difficult, as many rural areas do not have a health care provider nearby, most people who are poor can cannot afford to own a car, and public transport is often unreliable or impacted by weather conditions or other factors beyond the control of the patient. These same factors also impact the ability of a health care provider to visit individual patients, but in addition, each health care provider may have numerous patients who are in geographically disparate locations. This situation limits the number of patients a single health care provider can monitor in person to ensure the patient complies with a drug dosage regimen.

This waste in resources is even more egregious because the group of patients who takes the medicine in the appropriate manner is treated the same as the group of patients that regularly fails to take the medication in the appropriate manner. Both groups are required to be directly observed by the health care provider. The inventor has determined that significant resources can be redirected from observing patients to instead providing medicines to treat patients if patients who comply with the dosing regimen are permitted to self-administer the medicine. The inventor has developed pharmaceutical compositions and methods to determine whether or not a patient is taking the medicine.

The compositions and methods disclosed herein also may be useful in clinical drug studies to determine whether or not a study subject is taking the study drug in the clinical study. In a clinical study, drug efficacy will be determined from the outcomes of the study, which makes the ability to determine if a study enrollee has taken the study drug according to the dosing schedule critical for determining the success or failure of a new drug. If the study enrollees do not take the drug or do not take it according to the dosing regimen, the drug may not be effective in treating the condition, or results from the study may not accurately reflect the true efficacy of the drug being studied. For example, if the results of a study include too many enrollees who failed to comply with the drug dosing regimen, statistically significant results of the study may not be attained, and the resulting outcome may provide only a marginal benefit to the company's objective because the results provide limited value in assessing the drug's safety and effectiveness. In addition, studies with results based on a low number of study enrollees may cause regulatory authorities (such as the FDA) to require additional studies or make negative inferences about the outcome, both of which add cost to and may delay the approval of the product—a significant negative financial result for the company.

There are a number of compliance systems and dosage forms in the prior art. For example, U.S. Pat. No. 7,062,312 discloses an orally administrable medication composition that includes a visual marker. When the medication is orally ingested, the marker causes a coloration or discoloration of the oral and/or pharyngeal cavity of a subject. By visually observing the oral and/or pharyngeal cavity of the subject, one can determine whether medication has been ingested based upon the presence or absence of the coloration/discoloration. The '312 patent further explains that noncompliance is addressed by notifying the patient that compliance is being monitored and that should noncompliance persist, that information would allow a caregiver to alter the methods of medication delivery. For example, a child in school or daycare who requires daytime dosing of an antibiotic for recurrent ear infections could be given an antibiotic containing the marker. The child could then be checked for ingestion compliance immediately after scheduled ingestion, or if necessary, several hours after the scheduled ingestion. The verification could occur, for example, by visual inspection of the oral and/or pharyngeal cavity immediately after the delivery under natural light or several hours later by inspection under a light which causes fluorescence.

U.S. Pat. No. 6,068,981 is directed to a method of monitoring a therapeutic regimen in an animal. The method involves: a) providing to the animal a therapeutic compound and a detectable compound that passes into the bloodstream, excretory system, or other tissue or body fluid in detectable form; b) after a period of time, following step (a), sufficient for passage of a detectable amount of the detectable compound into the body fluid or tissue, collecting a sample of the fluid or tissue from the animal; and c) measuring or detecting the detectable compound, or a detectable metabolite thereof, in the sample, wherein the detectable compound involves one member of a specific binding pair, and detection is carried out using the second member of the specific binding pair.

U.S. Pat. No. 5,908,788 is directed to a method of monitoring compliance of a patient that has been placed on a medication maintenance program with a prescribed medication dosage by determining a normalized urine methadone concentration. According to the method, an unadulterated urine sample is obtained from the patient. The urine methadone concentration and urine specific gravity are measured. The normalized urine medication concentration is calculated as a function of the measured medication concentration in the urine and the urine specific gravity. The calculated normalized urine medication concentration is compared with an expected medication concentration value for the patient for the maintenance program prescribed to determine any significant differences therebetween as an indication of noncompliance. Alternatively, a urinary-parameter normalized urine medication concentration is calculated as a function of the measured medication concentration in the urine, the urine specific gravity and at least one selected pharmacokinetic parameter of the medication. The calculated urinary-parameter normalized urine medication concentration is compared with an expected medication concentration value for an average compliant patient for the maintenance program prescribed to determine any significant differences therebetween as an indication of noncompliance.

U.S. Pat. No. 5,776,783 is directed to a method of monitoring therapeutic agent consumption. The method includes quantitative compliance markers and associated methods for monitoring patient compliance with medication prescriptions associated with compliance markers to eliminate the need for specific quantitative relationships for each new drug tested. According to the method of monitoring compliance of a patient who has been placed on a medication maintenance program with a prescribed medication dosage, the method includes (a) physically associating a compliance marker with a prescribed medication dosage prior to ingestion, (b) obtaining a sample of the patient's urine, (c) measuring the concentration of the compliance marker and its metabolites in the urine and the urine specific gravity, (d) calculating a normalized urine compliance marker and its metabolite concentration as a function of the measured compliance marker and its metabolite concentration in the urine and the urine specific gravity adjusted to account for the difference between the urine measured specific gravity and a preselected reference urine specific gravity, and (e) comparing the normalized urine compliance marker and its metabolite concentration with an expected normalized urine compliance marker and its metabolite concentration for the amount of compliance marker prescribed, as an indication of compliance or noncompliance.

U.S. Pat. No. 6,421,650 is directed to a medication management system which includes three components to assist a patient to control, monitor and manage administration of prescribed medications. The system includes a patient component having a retrievable patient database of patient medical history, prior prescribed medications and current prescribed medications, and it includes a data transfer interface, e.g., a hardwired interface, such as an RS232 interface or infrared data transfer port. The system also includes a physician component having a retrievable physician's database of medication information and an input/output device enabling a prescribing physician to enter prescription information into the physician component. The physician's database is capable of receiving and storing patient data transferred from the patient component through said data transfer interface. The system finally also includes a pharmacist component resident on a pharmacist's computer. The pharmacist's computer is adapted to interface with the patient component to transfer prescription data to said pharmacist component. At least one of each of the physician component and the pharmacist component has the capability of searching a medication database to determine potential medication interactions with currently prescribed medications and identify those to the physician or pharmacist for selective downloading to the patient component so that the patient can be alerted to the potential interactions. The patient component has a scheduler which tracks a plurality of medication dose schedules and includes alarm functions to prompt a patient to take particular medications, reschedule them, and alert the patient to potential interactions between medications and/or provide caution information to the patient for administration of the medication.

U.S. Pat. No. 6,578,003 is directed to a method and apparatus for improving patient compliance with prescriptions that utilizes computer terminals to convert prescription information into electronic form as records for each patient. Each such patient record includes information about the patient from the prescription and the prescription itself. In addition, demographic information about the patient is obtained from other commercial databases and added to the patient record. Then a regression analysis is run on the patient records using the various data elements versus the compliance of the patient with the prescription to determine the relative importance of each variable in the prediction. The analysis is used to segregate the patients into demographic clusters and to associate champion intervention messages with each cluster. When a patient's prescription is entered in the system thereafter, the model is used to associate the patient with a cluster and to direct the champion message to that patient. Further, a regression analysis may be run on the patient data to create a model of likelihood of prescription compliance in general by the patient. The result is a probability equation that allows a score to be assigned to each record. Based on this score, the patients most likely to fail to comply with their prescription are sent the champion interventions. As new challenge interventions messages are created additional information is gathered and the regression analysis is re-run. If the challenge message is more successful, it is substituted as the new champion message. The results of these interventions are recorded and appended to the related patient record.

U.S. Pat. No. 7,415,447 is directed to an apparatus and method for prediction and management of participant compliance in clinical research. The system uses empirically derived algorithms to generate decision rules to determine participant noncompliance and fraud with research protocols in clinical trials allows for the identification of complex patterns of variables that detect or predict participant noncompliance and fraud with research protocol, including performance and enrollment goals, in the clinical trial. The data may be used to overall predict the performance of any participant in a clinical trial, allowing selection of participants that tend to produce useful, high-quality results. The present invention can also be used to monitor participant compliance with the research protocol and goals to determine preferred actions to be performed. Optionally, the invention may provide a spectrum of noncompliance, from minor noncompliance needing only corrective feedback, to significant noncompliance requiring participant removal from the clinical trial or from future clinical trials. The algorithms and decision rules can also be domain-specific, such as detecting non-compliance or fraud among subjects in a cardiovascular drug trial, or demographically specific, such as taking into account gender, age or location, which provides for algorithms and decision rules to be optimized for the specific sample of participants being studied.

U.S. Pat. No. 6,039,688 is directed to a therapeutic behavior modification program with a compliance monitoring and feedback system. The therapeutic behavior modification program, compliance monitoring and feedback system includes a server-based relational database and one or more microprocessors electronically coupled to the server. The system enables development of a therapeutic behavior modification program having a series of milestones for an individual to achieve lifestyle changes necessary to maintain his or her health or recover from ailments or medical procedures. The program may be modified by a physician or trained case advisor prior to implementation. The system monitors the individual's compliance with the program by prompting the individual to enter health-related data, correlating the individual's entered data with the milestones in the behavior modification program and generating compliance data indicative of the individual's progress toward achievement of the program milestones. The system also includes an integrated system of graphical system interfaces for motivating the individual to comply with the program. Through the interfaces, the individual can access the database to review the compliance data and obtain health information from a remote source such as selected sites on the Internet. The system also provides an electronic calendar integrated with the behavior modification program for signaling the individual to take action pursuant to the behavior modification program in which the calendar accesses the relational database and integrates requirements of the program with the individual's daily schedule, and an electronic journal for enabling the individual to enter personal health-related information into the system on a regular basis. In addition, the system includes an electronic meeting room for linking the individual to a plurality of other individuals having related behavior modification programs for facilitating group peer support sessions for compliance with the program. The system enables motivational media presentations to be made to the individuals in the electronic meeting room as part of the group support session to facilitate interactive group discussion about the presentations. The entire system is designed around a community of support motif including a graphical electronic navigator operable by the individual to control the microprocessor for accessing different parts of the system.

US 2005/0267356 is directed to packages of medications that have features for improving patient compliance with taking the medication. According to the abstract of the published application, the method involve generating and storing an identifier for a specific dosage instance of a specific patient, and creating a package that includes a mechanism for conveying the identifier. Once the package is created, a set of one or more medications that are prescribed to be taken by the specific patient at the specific dosage instance are placed in the package. The set of medications are placed within the package in a manner that prevents the identifier from being perceived from the mechanism until the package is opened. Once opened, the identifier is perceived and communicated back to an automated compliance system.

Although these systems describe various systems for detecting whether or not a patient has taken a pharmaceutical, the system require direct observation and therefore does not alleviate the problem of wasted resources spent in monitoring patient compliance. Further, the systems are complicated and do not provide a simple method that is easily implemented to determine compliance with a drug dosing regimen. Further, because the patient can easily discern the result of the compliance determination, they can also easily provide a false report of compliance that is indistinguishable from a true report.

SUMMARY

In one general aspect, a pharmaceutical dosage form has a distinguishing characteristic and an identifier associated with the dosage form. The distinguishing characteristic is assigned from a limited set of distinguishing characteristics and is determined upon oral administration of the dosage form, or after injection or other non-oral administration of the dosage form. The identifier is associated with the dosage form and with the distinguishing characteristic. The identifier is associated with only one distinguishing characteristic but the distinguishing characteristic may be associated with multiple identifiers.

Embodiments of the dosage form may include one or more of the following characteristics and features. For example, the distinguishing characteristic may be an organoleptic property. The organoleptic property may be a flavor. The organoleptic property may be a color. The organoleptic property may be a texture.

In another example, the distinguishing characteristic may be a chemical compound detectable in breath, bodily fluids, or tissues after ingestion, or injection or other non-oral administration of the dosage form.

The identifier associated with the dosage form may be one or more alpha-numeric characters. The identifier may be randomly generated. The identifier may be associated with the distinguishing characteristic. The identifier may be placed on an article associated with the dosage form and the article associated with the dosage form may be the packaging or package insert accompanying the dosage form. The identifier may be unique.

In another general aspect, there is provided a method for monitoring compliance with a pharmaceutical dosing regimen. The method may include:

providing a dosage form having a distinguishing characteristic and an identifier;

storing the identifier and distinguishing characteristic in a look up table in a database on computer readable memory, wherein the identifier and distinguishing characteristic are stored in the database in a relationship;

providing software stored on computer readable memory in which the software is configured to receive a patient identifier, the dosage form identifier and the distinguishing characteristic;

upon receipt of the patient identifier, dosage form identifier and distinguishing characteristic in the software, determining if that provided dosage form identifier is associated in the database with that provided distinguishing characteristic.

In the method, the distinguishing characteristic is assigned from a limited set of distinguishing characteristics and is determined upon oral or other administration of the dosage form. The identifier is associated with the dosage form and with the distinguishing characteristic. The identifier is associated with only one distinguishing characteristic but the distinguishing characteristic may be associated with multiple identifiers.

Embodiments of the method may include one or more of the following features or those described above. For example, the look up table or at least a portion of the look up table may be further provided on paper. Determining if that provided dosage form identifier is associated in the database with that provided distinguishing characteristic may provide a measure of compliance.

In another general aspect there is provided a method for monitoring compliance with a pharmaceutical dosing regimen. The method includes the step of providing a dosage form comprising an active ingredient, a compound capable of being detected, and one or more pharmaceutical acceptable carriers; the step of providing a test strip to a patient, the test strip having at least two regions, wherein each region can be distinguished from another region on the test strip and at least one region includes a reagent that can be activated by the compound capable of being detected when the compound contacts the reagent; the step of, after administration of the dosage form to a patient, contacting the test strip with a body fluid or substance containing the compound capable of being detected; and the step of reporting the region activated on the test strip or the lack of a region being activated on the test strip.

Embodiments of the method may include one or more of the features described above or listed below. For example, the active ingredient may be the compound capable of being detected. The dosage form may be provided with an indentifier.

The details of various embodiments of the invention are set forth in the accompanying drawings and the description below. Other features and advantages of the invention will be apparent from the description, the drawings, and the claims.

DESCRIPTION OF THE DRAWINGS

FIG. 1 is a plan view of a drug compliance monitoring system

DETAILED DESCRIPTION

Figure 2:
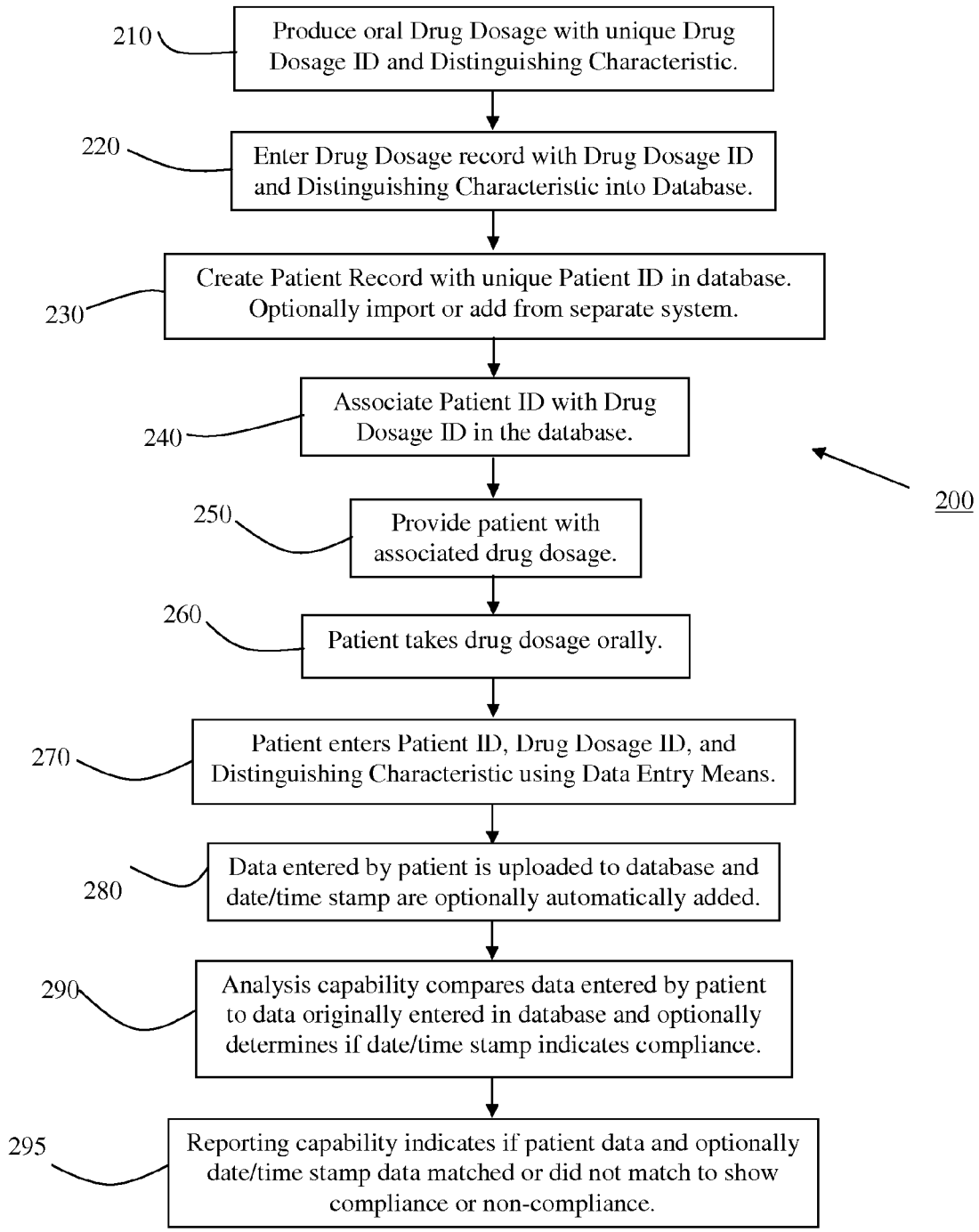
FIG. 2 is a flow chart illustrating a method for monitoring drug compliance

The inventor has developed a drug compliance monitoring system to address the problems described above that monitors compliance with a drug regimen by providing a drug dosage form that has an ID and a separate characteristic that can only be determined by a patient when the patient takes the medication orally, or after other administration of the dosage form. The drug compliance monitoring system further includes a means for the patient to provide the ID of the drug dosage to a software-based monitoring system, to specify the characteristic of the drug dosage to the software-based monitoring system, and to associate the patient's patient ID with this data in the software-based monitoring system. The monitoring system includes a table that correlates the ID of the drug dosage form with the characteristic in such a way that there is only one characteristic associated with that drug dosage form ID. As used herein, drug dosage form ID, pill ID, and dosage form identifier, etc. are used interchangeably to indicate the ID associated with or on the dosage form or pill.

The means for the patient to provide the ID of the drug dosage form and the characteristic is generally a distance communication device or system. As described in more detail below, a distance communication device or system is a device that allows an entity at a first location (e.g., a patient in a small village in Malawi) to communicate with a database at a second location (e.g., a clinic in a larger village, town or city in Malawi or other country). In one implementation, the distance communication device and system can be as simple as a cell phone in the village that treatment recipients use to communicate with a server on which the database resides in the second location. In another implementation, the distance communication device and system is a computer workstation at an individual's residence with a wireless connection to the internet and a camera or scanner connected to the computer for transmitting optical information about the dosage form and the characteristic of the drug dosage to a database residing on a distant server with automated voice prompts to allow the treatment recipient the option of transmitting the information easily from the privacy of their residence. It should be understood from the above description of the distance communication device and system that the invention is not intended to be limited to specific hardware and software configurations.

The drug compliance monitoring system also may include the optional abilities to evaluate patient compliance with a drug dosage regime, provide the results of the evaluation to interested parties such as a clinical drug study or health care provider, provide assistance such as automated alerts to patients to help improve compliance and provide recommendations to health care providers, clinical drug study organizations or other entities to make the best use of their resources. The invention can take numerous different forms and can be used in a variety of situations that require a means of verifying that a patient or enrollee has taken a drug dosage according to a defined drug regimen. In general, the systems described herein take advantage of distance communications devices and systems to make these advantages and features possible. The invention is described in more detail below.

In one aspect, the inventor has developed a pharmaceutical dosage form that has an active ingredient, one or more pharmaceutically acceptable carriers in which at least one of the carriers has a distinguishing characteristic, and an identifier. The distinguishing characteristic is assigned from a limited set of distinguishing characteristics that are determined upon oral administration of the dosage form, e.g., flavor. The identifier is associated with the dosage form and with the distinguishing characteristic, the identifier being associated with only one distinguishing characteristic. One suitable distinguishing characteristic is a flavor, such as a sweet flavor or taste, selected from the set of sweet, salty, sour and bitter. The use of flavors as pharmaceutically acceptable carriers in the pharmaceutical arts is well known to one of ordinary skill in the art. The identifier can be made up of a six digit character string alone or in combination with the dosage form color or some other property of the dosage form. For example, if a dosage form is yellow and has a six digit character string printed on its outer surface in the form of 12676Q, the identifier can be Y12676Q where Y indicates is the pill color.

Other color pills could be used and a representative letter of the color used in the identifier, e.g., blue (B), red (R), green (G), etc.

There also is provided a look up table, in electronic or paper form, that correlates the identifier to the distinguishing characteristic. The look up table is not generally in the possession of the patient taking the pill. In this example, the identifier Y12676Q is associated with only one distinguishing characteristic, in this case, sweet. In this manner, by using the identifier and distinguishing characteristic in combination with a look up table, the system described herein provides the ability to verify that a patient has taken the dosage form. Because the patient does not have access to the table correlating pill ID with flavor, the system prevents the patient from fraudulently having the ability to enter the correct flavor without at least putting the pill in their mouth.

Figure 5:
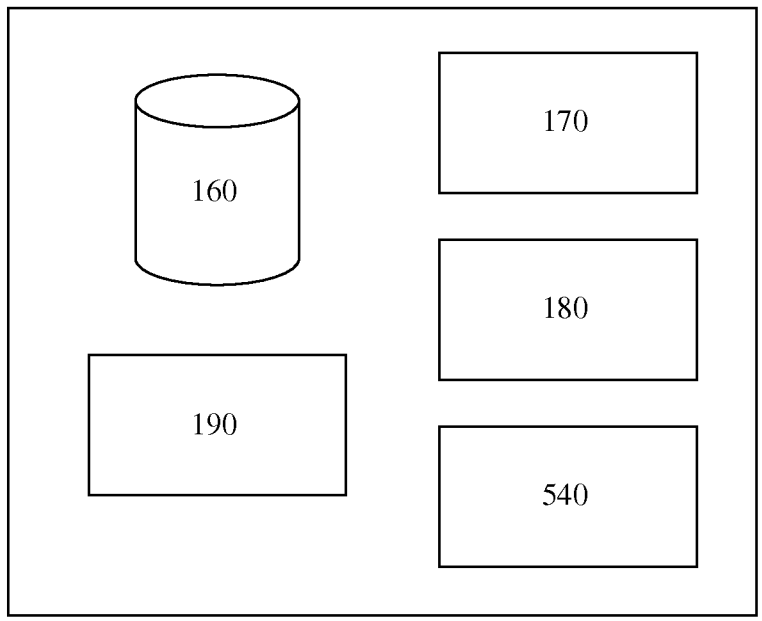
FIG. 5 is a flow chart showing a plan arrangement of the software-related components of the system.

Referring to FIG. 1, in one basic implementation, the drug compliance monitoring system 100 can be implemented using compliance monitoring software 155 residing on a server 150. The compliance monitoring software includes the compliance monitoring software 155, a database 160 on computer readable memory with tablets for patient ID, drug dosage ID, and distinguishing characteristics; a data analysis module 170 stored on computer readable memory, a reporting module 180 stored on computer readable memory, and a user interface 190 that may include a display. The arrangement of the software components in this arrangement is further illustrated in FIG. 5.

In using the system 100, first, a manufacturer produces a drug dosage batch in the form of one or more pills 110 intended for oral administration. Each pill includes one or more active ingredients and one or more pharmaceutically acceptable carriers. An example of a dosage form that has more than one active ingredient includes those HIV treatments that include multiple active ingredients, e.g., a combination of abacavir sulfate, lamivudine, and zidovudine. Each pill in the batch is given a characteristic that is easily distinguishable by a patient when the patient takes the drug orally; for example, the distinguishing characteristic may be a sweet, salty, bitter or sour flavor applied to an outer coating or as an outer coating. In one implementation, the distinguishing characteristic is an organoleptic property, such as flavor, smell or texture. Optimally, the distinguishing characteristic is one that is recognized only upon oral administration. For the purposes of this basic implementation example, the pill has an outer coating with a sweet flavor and a core with the active ingredient(s) and pharmaceutical acceptable carrier(s). The flavors selected for the distinguishing characteristic might be culturally specific. The distinguishing characteristic can also be a texture such as gritty or smooth that is applied to a drug dosage outer coating or is under an outer coating such that the texture can be determined only upon oral administration and dissolution of the outermost coating. In another form, the distinguishing characteristic might be a sub-coating color that is revealed when the outer coating dissolves upon insertion into the patient or enrollee's oral cavity and subsequent exposure to saliva.

Exemplary formulations of dosages form prepared according to one aspect of the invention are as follows. It should be noted that these examples merely provide guidance for some applying aspects of the inventions disclosed herein and should not be construed to be limiting to the various inventions disclosed herein.

Example 1

Pharmaceutical Formulation of 100 mg Tablets of Lamivudine

| Ingredient | Amount per tablet |
| --- | --- |
| Lamivudine | 100.00 mg |
| Microcrystalline cellulose NF | 189.5 mg |
| Sodium Starch Glycolate NF | 9.0 mg |
| Magnesium Stearate NF | 1.5 mg |
| Total Weight | 300.00 mg |

The lamivudine, microcrystalline cellulose and sodium-starch glycolate are sieved and blended in a V-blender for about 15 minutes. The sieved magnesium stearate is then added and blending continued for a further 2 minutes. The blend is compressed in standard tabletting equipment and then film coated with an aqueous suspension of grey Opadry and an organoleptic excipient to produce aesthetically acceptable tablets. The organoleptic excipient may be a sweet, salty, bitter or sour flavor excipient.

Example 2

Pharmaceutical Formulation of 300 mg Tablets of Lamivudine

| Ingredient | Amount per tablet |
| --- | --- |
| Lamivudine | 300.00 mg |
| Microcrystalline cellulose NF | 279.0 mg |
| Sodium Starch Glycolate NF | 18.0 mg |
| Magnesium Stearate NF | 1.5 mg |
| Total Weight | 600.00 mg |

The lamivudine, microcrystalline cellulose and sodium-starch glycolate are sieved and blended in a V-blender for about 15 minutes. The sieved magnesium stearate is then added and blending continued for a further 2 minutes. The blend is compressed in standard tabletting equipment and then film coated with an aqueous suspension of grey Opadry and an organoleptic excipient to produce aesthetically acceptable tablets. The organoleptic excipient may be a sweet, salty, bitter or sour flavor excipient.

Examples 3A-C

Pharmaceutical Formulation of 250 mg Tablets of Lamivudine, Zidovudine, Abacavir Sulfate The following formulations A, B and C are prepared by wet granulation of the ingredients with a solution of povidone, followed by addition of magnesium stearate and compression.

Formulation 3A

| Ingredient | Amount per tablet |
|---|---|
| Lamivudine, Zidovudine, Abacavir sulfate | 250.00 mg |
| Lactose BP | 210.0 mg |
| Povidone BP | 15.0 mg |
| Sodium Starch Glycolate NF | 20.0 mg |
| Magnesium Stearate NF | 5 mg |
| Total Weight | 500.00 mg |

Formulation 3B

| Ingredient | Amount per tablet |
|---|---|
| Lamivudine, Zidovudine, Abacavir sulfate | 250.00 mg |
| Lactose BP | 150.0 mg |
| Avicel PH 101 | 60.0 mg |
| Povidone BP | 15.0 mg |
| Sodium Starch Glycolate NF | 20.0 mg |
| Magnesium Stearate NF | 5 mg |
| Total Weight | 500.00 mg |

Formulation 3C

| Ingredient | Amount per tablet |
|---|---|
| Lamivudine, Zidovudine, Abacavir sulfate | 250.00 mg |
| Lactose BP | 200.0 mg |
| Povidone BP | 5.0 mg |
| Starch | 50.0 mg |
| Magnesium Stearate NF | 4.0 mg |
| Total Weight | 509.00 mg |

The compositions of Examples 3A-C are compressed in standard tabletting equipment and then film coated with an aqueous suspension of Opadry, or other coating material, with an organoleptic excipient to produce aesthetically acceptable tablets. The organoleptic excipient may be a sweet, salty, bitter or sour flavor excipient.

Examples 3D-E

Pharmaceutical Formulation of Tablets of Lamivudine, Zidovudine, Abacavir Sulfate The following formulations, Examples 3D and E, are prepared by direct compression of the admixed ingredients. The lactose in formulation E may be of the direct compression type (Dairy Crest—"Zeparox").

Formulation 3D

| Ingredient | Amount per tablet |
|---|---|
| Lamivudine, Zidovudine, Abacavir sulfate | 250.00 mg |
| Pregelatinized Starch NF | 150.0 mg |
| Total Weight | 400.00 mg |

Formulation 3E

| Ingredient | Amount per tablet |
|---|---|
| Lamivudine, Zidovudine, Abacavir sulfate | 250.00 mg |
| Lactose BP | 150.0 mg |
| Avicel | 100.0 mg |
| Total Weight | 500.00 mg |

The compositions of Examples 3D-E are directly compressed in standard tabletting equipment and then film coated with an aqueous suspension of Opadry, or other coating material, with an organoleptic excipient to produce aesthetically acceptable tablets. The organoleptic excipient may be a sweet, salty, bitter or sour flavor excipient.

Example 4

Controlled Release Pharmaceutical Formulation of Tablets of Lamivudine, Zidovudine, Abacavir Sulfate The formulation is prepared by wet granulation of the ingredients with a solution of povidone followed by the addition of magnesium stearate and compression.

Formulation 4

| Ingredient | Amount per tablet |
|---|---|
| Lamivudine, Zidovudine, Abacavir sulfate | 500.00 mg |
| Hydroxypropyl methylcellulose | 112.0 mg |
| Lactose BP | 53.0 mg |
| Povidone BP | 28.0 mg |
| Magnesium Stearate NF | 7 mg |
| Total Weight | 700.00 mg |

The composition of Example 4 is compressed in standard tabletting equipment and then film coated with an aqueous suspension of Opadry, or other coating material, with an organoleptic excipient to produce aesthetically acceptable tablets. The organoleptic excipient may be a sweet, salty, bitter or sour flavor excipient. Drug release from the dosage form takes place over a period of about 6-8 hours and is complete after 12 hours.

Example 5

Pharmaceutical Formulation in the Form of a Syrup Containing Lamivudine, Zidovudine, Abacavir Sulfate

Formulation 5

| Ingredient | Amount per 5 ml |
| --- | --- |
| Lamivudine, Zidovudine, Abacavir sulfate | 250.00 mg |
| Organoleptic flavoring solution | 1.5 mg |
| Glycerol | 2.0 mg |
| Sodium benzoate | 0.005 mg |
| Purified water | 7 mg |

The active ingredient mixture is dissolved in a mixture of the glycerol and most of the purified water. An aqueous solution of the sodium benzoate is then added to the solution, followed by addition of an organoleptic flavoring solution. A flavor optionally may be added. The volume is made up with purified water and mixed well.

Example 6

Pharmaceutical Formulation in the Form of a Freeze-Dried Dosage Form with an Active Ingredient A freeze-dried, orally disintegrating dosage form may be used as follows. It will be appreciated that the precise therapeutic dose of the active ingredient will depend on the age and condition of the patient, the nature of the condition to be treated, and the active ingredient(s) and dosage selected. The following non-limiting example further illustrates one application of the invention as a freeze dried dosage form. It should be noted that 4 and 8 mg of active ingredient is exemplified. More or less of the active ingredient may be used, such as 100 mg of active ingredient.

Formulation 6

| Ingredient | Amount per 125 mg tablet | Amount per 250 mg tablet | % w/w |
| --- | --- | --- | --- |
| Active ingredient(s) | 4.00 | 8.0 | 3.2 |
| Gelatin Pharm Eur/USP | 5.0 | 10.0 | 4.0 |
| Mannitol Pharm Eur/USP | 3.75 | 7.5 | 3.0 |
| Aspartame | 0.625 | 1.25 | 0.5 |
| Strawberry Flavouring Aid | 0.125 | 0.25 | 0.1 |
| Sodium Methylhydroxybenzoate | 0.0555 | 0.111 | 0.0044 |
| Sodium Propylhydroxybenzoate | 0.0070 | 0.014 | 0.0056 |
| Purified water | qs to 125 mg | qs to 250 mg | qs to 100% |

Solid dosage forms that disintegrate rapidly in the mouth, such as freeze-dried solid dosage forms, are described in UK Patent Nos. 1548022, 2111423, 2119246, 2114440, 2111184, 2120370, and U.S. Pat. Nos. 5,046,618, 6,417,191 and 5,188,825, all incorporated herein by reference. The components of the composition above are mixed together as, for example, described in the patents incorporated herein by reference above. The suspension is then poured into blister molds. For 4 mg unit doses, the fill weight is 125 mg; for 8 mg unit doses the fill weight is 250 mg. If more active ingredient is desired, the weight of the aqueous composition poured into a mold (the wet fill weight) may be in the range of 50 to 750 mg, such as 100 to 500 mg, for example 125 or 250 mg, with the amount of active ingredient(s) proportionally increased. The suspension is frozen, freeze-dried, and then sealed with a covering sheet adhered to the mould, as for example described in the patents incorporated herein by reference.

To be capable of being disintegrated rapidly, the freeze-dried dosage form may comprise a network of pharmaceutically acceptable water soluble or water-dispersible carrier material, conveniently as described in the patents incorporated herein by reference above, for example, in UK Patent No 1548022. Suitable materials to act as a carrier material include, for example, gelatin (including partially hydrolysed gelatin), polysaccharides such as hydrolysed dextran, dextrin and alginates (e.g. sodium alginate) or mixtures of the above mentioned carriers with each other with other carrier materials such as polyvinyl alcohol, polyvinylpyrrolidine or acacia.

Conventional excipients which may also be employed in the freeze-dried dosage forms according to the invention include preservatives, flavoring aids, coloring aids, sweeteners, fillers, and mixtures thereof. Suitable sweeteners include, for example, sugars such as sucrose, lactose and glucose; cyclamate and salts thereof; saccharin and salts thereof; and aspartame. In place of a sweetener, a bitter, sour or salty excipient can be used to give that flavor upon administration.

Active ingredients other than those specifically listed above may be used in the formulations. For example, the drug may be an HIV, tuberculosis, or antibiotic agent.

As examples of the organoleptic excipients described in the above examples, the sweet excipient may be dextrose, sacchrin, mannitol, sorbitol, glucose, sucrose, or xylitol, as are known in the art. Other sweet compounds generally are polyhydroxyl compounds, polyhalogenated compounds, and alpha amino acids. A sour excipient can be citric acid, a salt excipient can be sodium chloride and a bitter excipient can be caffeine.

The following correlation has been reported for flavoring pharmaceuticals:

| | |
| --- | --- |
| Salty | Butterscotch/Maple |
| Bitter | Wild Cherry/Licorice |
| | Chocolate Mint |
| Acrid/Sour | Raspberry/Fruit |
| | Berry/Acacia Syrup |

Other sweet, sour, salty and bitter excipients are known in the art or are readily accessible through a review of the *Handbook of Pharmaceutical Excipients*. Reference to formulation of dosage forms including an organoleptic agent are found, for example in U.S. Pat. No. 6,417,191, U.S. Pat. No. 6,063,802, and U.S. Pat. No. 5,905,082, the contents of which are incorporated herein in their entirety by reference for disclosing techniques of forming dosage forms.

The oral drug dosage can take many forms and the inventor does not intend to limit the invention to any particular dosage form. The drug dosage form may be an oral drug dosage with an external coating containing the distinguishing characteristic; an oral dosage with a sub-coating that contains the distinguishing characteristic but the characteristic is readily recognized upon oral administration; a solid oral dosage with the distinguishing characteristic such as a flavor included as a water-soluble or water-dispersible excipient; an orally disintegrating tablet in which the distinguishing characteristic is included with the excipients used in formulating the tablet; a packet with a powder with the distinguishing characteristic such as a flavor mixed in as the excipient; or a liquid with a distinguishing characteristic such as a flavor in a single dosage form such as a small tube or packet. Thus, the invention should be understood to be applicable to at least tablets, capsules, caplets, soft gelatin capsules, oral solutions, injectables, etc., and reference to one type of dosage form is not intended to exclude applicability to a different type of dosage form. Similarly, the dosage forms may be immediate release, delayed release, extended release, controlled release, etc. because the nature of the drug release is not expected to interfere with the ability of the patient to identify the distinguishing characteristic associated with the dosage form. These dosage forms are well known in the art by one of skill in the art and can be practiced with routine experimentation.

As part of the manufacturing process, the pill also has or may have an ID printed on its outer coating. However, the pill ID may be associated with the pill by some other means such as printing the pill ID on the individual pill packaging; for example, on the packet that contains the drug dosage in a powder form, on the tube that contains a liquid form of the drug dosage, on the foil of a pouch that contain an individual dosage in a pill form, on a vial that contains an injectable form of the drug; or on the label of a plastic pill container that contains an individual dosage in a pill form.

While an ID that is easily viewable by the patient is an easily implemented option, the inventor anticipates that a number of other implementations are possible to associate an identifier with the dosage form and allow that identifier to be recognized. For example, in one implementation, the dosage form can be printed with a bar code or similar identifier and a smart phone provided to the patient. In this implementation, the smart phone is provided with a bar code reader application such that the tablet can be positioned in front of the phone and the bar code scanned. In this manner, the possibility of data entry error by the patient is reduced. In a related implementation, patterns of colors can be used in place of the bar code and the smart phone can be provided with an application for reading and processing color coding. In another related implementation, the smart phone can be provided with an optical character recognition application that will read an alpha-numeric code printed on the dosage form or article associated with the dosage form. These various forms of retrieving the identifier from the dosage form or article associated with the dosage form are not intended to be limiting but instead to show the variety of methods and technology that can be used to accurately capture the identifier associated with the dosage form.

In one implementation, it also should be understood that the pill ID is not to be confused with other forms of identifying a batch of pills or something that is not at the level of the pill. Similarly, the pill ID also should not be confused with other forms of identifying pharmaceuticals, such as NDC code, batch record, etc. that are commonly found used in the pharmaceutical industry. The objective should be to identify a particular pill and ensure that it can be correlated with a distinguishing characteristic.

While the distinguishing characteristic is unlikely to be a unique form of identification (e.g., the flavor or color is likely to be selected from only one of a number of flavors or colors), the pill ID is not so limited. In combination, however, the characteristic associated with the pill and pill ID allows the use of a look up table, either in the form of computerized or electronic data and/or a paper copy of the table correlating the pill ID to a single characteristic from a number of the characteristics. In other words, if the pill has ID number Q458793 associated with it and that pill has a bitter flavor, the look up table correlating ID number with flavor would have a single entry for the pill ID and that ID would be associated with bitter for the flavor. In this manner the combination of the pill ID number and the distinguishing characteristic functions as a dual-code system that allows the combination to be used in conjunction with the look up table to verify patient compliance with a dosing regimen.

Optimally, for a given therapeutic agent, there would be a single use of the pill ID number. However, in some implementations, it is possible to use pill ID numbers more than once if necessary. For example, the pill ID number may be a combination of letters and numbers that may provide enough units of the drug to allow production of two years worth of the drug before the pill ID numbers repeat. Assuming two years of shelf life for the drug, the number of characters used in the pill ID number could be selected to allow two years worth of product to be made before the pill ID numbers repeat. A reason that the manufacturer might attempt to reduce the number of characters in the pill ID number is to increase their size on the pill to make the ID easier to read. In this way, it is expected that the correlation between pill ID number and distinguishing characteristic will be configured such that the likelihood that pill ID numbers would repeat at the same time is within an acceptable level for the therapeutic agent being used or tested.

In addition, as part of the production process, the pill ID and the distinguishable characteristic of the pill are automatically recorded and electronically correlated with each other in the manufacturer's database or in some other computer-readable storage. This correlation can be in the form of a look up table that is stored on hardware or software. The correlation also can be in the form of a simple listing on paper, e.g., a print out of portions of the table or all of the table. Although the data may be stored on software or hardware under the manufacturer's control, the manufacturer may transfer some or all of the data to other entities, such as a third party tracking service that is accessed by interested parties to verify the data as needed, or to a clinic or non-governmental organization (NGO) to which the pills are provided, etc. It should be clear, therefore, that there are no limitations on where the data resides and the location may vary based on local, national and international privacy laws, business arrangements between the manufacturer, NGO, government entity, healthcare provider or other interested organization involved in ensuring patient compliance in the administration of the dosage forms.

The manufacturer then distributes the pill to an entity (a drug dispensing entity 105) such as a public health program that provides a drug to patients 120 as part of its program to help treat an illness, a clinical research organization (CRO) that conducts a clinical study on behalf of a drug developer such as a pharmaceutical company, or some other entity responsible for ensuring the pill is administered to a patient or drug study enrollee. When the manufacturer distributes the drug, it also provides the correlated data for each drug dosage (the pill ID and distinguishing characteristic), or access to the correlated data. The manufacturer may provide the correlated data directly to the receiving entity using any one of a number of possible methods. For example, the manufacturer may send the data in an excel spreadsheet attached to an email; upload the data to an information system the receiving entity uses such as a medical record system; or mail the data in a Microsoft Excel spreadsheet or comma- or tab-delimited text file that has been saved to a CD, DVD USB drive or some other portable media storage device. In some implementations, the data may be in the form of print outs of the table that is tailored to provide each receiving party only that data that is related to their patients. Alternatively, the manufacturer may send the data to the compliance monitoring system software 155 using the aforementioned methods for sending to the receiving entity, or through an electronic connection that stores in directly in a database 160 that is hosted on a server 150.

It also should be understood that the manufacturer may not wish to transfer control of the correlating data to an entity outside the control of the manufacturer. As should be recognized, the manufacturer has an interest in ensuring that the integrity of the correlating data is not compromised or violated. For example, if the data is provided to a clinic, and a hacker accesses that data, the data can be made available, e.g., over the internet, and from that time forward the manufacturer and healthcare provider must question the validity of all patient entries into the system. To address this concern, the manufacturer may share only part of the data with the healthcare provider, use a trusted third party to administer access to the data, or permit access to the data only through its own systems.

The receiving entity might dispense the pill directly to a patient 120. Alternatively, the receiving entity might further distribute the pill to another entity such as a health clinic, physician, public health nurse, field health worker or other entity to dispense the pill to the patient 120. For example, in the case of an international public health program, the manufacturer might distribute the drug to the public health program that is based in the United States. In turn, the public health program might distribute the pill to an entity that lives in relative close proximity to the patient; for example, the physician, health clinic, public health nurse, health field worker, or other entity approved by the public health program to dispense the drug on behalf of the program. In turn, this entity dispenses the pill to the patient 120.

In this step, a drug dispensing entity 105 dispenses the pill to a patient 120, along with several additional pills that also have pill IDs and one of several possible distinguishing characteristics that the patient 120 can only determine by taking the pill orally. Although it is optimal that the distinguishing characteristic be recognized only upon oral administration it is also possible that other forms or means of recognizing the distinguishing are possible. For example, the dosage form may have a texture that is recognized upon removing from a blister package. As such, while optimal that the patient actually be orally administered the dosage form to allow the patient to determine the unique characteristic, other means of determining the characteristic are possible.

Continuing with the above example of the patient 120 receiving several pills, the patient may have ten pills of which three are salty flavored, two are bitter flavored, one is sweet flavored and four are sour flavored. Each pill may have a pill ID with non-limiting sample IDs being 37A66, JJ178, AHG-BTT, and 339978. The patient 120 will have a unique patient ID that is associated with the patient's information in an electronic patient record and that the compliance monitoring system can use to track the compliance of the patient 120 with respect to the drug dosage regimen. The patient 120 will be informed of this patient ID. For example, in one implementation the patient ID might be part of an electronic patient record contained in an information system such as an electronic medical record (EMR) system that the physician or clinic 105 who dispenses the pill to the patient 120 might use. In another implementation the patient ID might be part of a patient record in a table in the database 160 of the compliance monitoring system that the entity that dispenses the drug to the patient can access and update in some way. In another implementation the patient ID might be part of an electronic patient record in an information system that the entity who receives the pill from the manufacturer can update or alternatively allow the entity that dispenses the pill directly to the patient 120 to update. In yet another implementation the patient ID might be part of a patient electronic record that is part of an information system the CRO uses to track the patient 120 if the patient is a drug study enrollee. In yet another implementation, the patient ID may be the patient's cell phone or telephone number. Many systems that are accessed by a telephone have the ability to recognize a telephone or cell phone number. As such, the telephone number of the patient can be assigned as the patient ID, and that ID recognized when the patient uses a cell phone to contact the system. If the patient were to use a different cell phone to access the system, the patient could be prompted to verify the number as the patient ID or enter a different number as the patient ID.

When the patient 120 receives the pill, the patient is instructed on the appropriate dosing regimen, and specifically the date and time a pill should be taken. The date and time of the dosing regimen is recorded in the compliance monitoring system and is in some way associated with the patient ID. The patient 120 might be instructed to take a specific pill at a specific date and time or might be instructed in a more general way to take one of the pills at a date and time that reflects the drug dosing regimen. It should be understood that the concept of time as used in this example may refer to an interval of time or a particular part of the day. Thus, for a pill taken thrice daily, the patient can be instructed to take the pill every eight hours; at breakfast, lunch and dinner; at 8:00 am, 4 PM and midnight; etc. As a consequence the time of the dosing regimen entered into the system can be in the form of TID or thrice daily rather than a precise time, e.g., 8:30 am. In any event, the time provided into the system is not limited to a particular format but instead can be a precise time, a dosage regimen, an interval, etc.

In the next step, the patient 120 takes the pill orally. The patient notes by writing down or in some other way remembering the pill ID so that after taking the pill orally, the patient does not lose the pill ID information if, for example, the pill ID is printed on the pill's outer coating. The patient 120 tastes the flavored coating of the pill, or if the distinguishing characteristic is not a flavor, experiences and notes the distinguishing characteristic. Again, as described above, requiring oral administration of the dosage form to determine the flavor is merely one optimal means to obtain that information, and other means may be operational and can be used in the system described herein.

Next, the patient enters the data into the database of the compliance monitoring system software 155 using some data entry means 130. For example, the patient can call an automated phone service and uses the phone keypad or voice-activated entry to enter the data upon prompts from the automated phone service. With an automated phone service as the data entry means, the patient could take the pill, then call a toll-free number that connects to an automated phone system that prompts the patient 120 to enter the patient ID upon hearing the statement, "At the tone, enter your patient ID, followed by the pound sign." The patient would then enter the patient ID and press the pound sign (#). Then the system might continue, "At the tone, enter the ID printed on your pill or on the packaging that contained your pill. When you are finished, press the pound sign." The patient would then enter the pill ID and press the pound (#) sign. Then the system might continue, "After putting the pill in your mouth, select from the following options to indicate the flavor of the pill: Press 1 if the flavor is salty. Press 2 if the flavor is sweet. Press 3 if the flavor is sour. Press 4 if the flavor is bitter." The patient 120 would then press the number that corresponds to the flavor tasted after taking the pill orally. The system might then say, "Press the pound sign or hang up to submit your responses to the Drug Compliance Monitoring System." The patient 120 would then press the pound (#) sign, which would cause the system to automatically record the data into the database 160 of the compliance monitoring system software 155. Such phone based data entry systems are well known in the art and the details of their workings are not repeated here.

Alternatively, the data entry means 130 could be an application-based interface, browser-based user interface or a Web-based user interface or web-based or electronically readable form that the patient accesses from a laptop, desktop computer or smart phone with a wireless connection to the Internet. Of course, the data entry means does not need to be a device as sophisticated as a smart phone but may be a conventional cell phone or other land line. These data entry means have the common aspect of being useful for distance communication and can all be termed "distance communication devices" based on their ability to be used for communicating with a different location than the person making the call.

In using a connection over the Internet, the patient 120 could enter the URL or in some other way open the user interface or web-based form, enter the patient ID and pill ID, and after taking the pill, indicate which distinguishing characteristic tasted or experienced by selecting it from a list of the possible distinguishing characteristic options. For example, if the pill had a sweet flavored outer coating with possible flavors of "salty," "sweet," "sour," or "bitter," and the patient 120 tasted a sweet outer coating, the patient would select "sweet." The patient 120 would then submit the patient-entered data electronically to the database 160 of the compliance monitoring system software 150.

Although a simple implementation requires the patient to manually enter the pill ID into the cell phone, more sophisticated systems can be used. For example, the patient can be provided a cell phone with an optical recognition application that recognizes the pill ID, bar code, color code or other visually-based ID. Similarly, if the characteristic associated with the dosage form is a color, the cell phone can also have an application that uses the camera function to take a picture of the patient's open mouth, process the picture to determine a color within the mouth and report that color along with the dosage form ID and patient ID.

Submitting the data could occur in many possible ways, for example, by clicking a button in an application user interface that then connects to the Internet and transmits the data to the compliance monitoring system software, clicking a button in an Internet-connected browser-based user interface or web-based form that submits the data to the compliance monitoring system software, or saving and emailing an electronically readable form that the compliance monitoring system software can read to import the patient-entered data.

Upon submission to the compliance monitoring system software 155, an optional date and time stamp is added to the data entered by the patient 120 to indicate the time at which the patient 120 took the pill or at least entered the data into the system. If the patient 120 does not submit any data to the database, then the system will update the patient's record to show that the patient did not enter any information.

At this point in the process, the database 160 of the compliance monitoring system software 155 contains the original data associated with the pill by the manufacturer (the unique pill ID and the distinguishing characteristic); optionally the date and time the patient was instructed to take the pill; and the data entered by the patient 120 (the patient ID and the unique pill ID and the distinguishing characteristic of the specific pill the patient took orally), optionally including a date and time stamp that indicates when the patient took the pill. At a minimum, the database would include the pill information and whether or not the patient's entry was correct. At the next level, the database would include the date on which the patient entered the information. At the next level, the database would include the dosing regimen so the system can compare whether or not the patient took the pill when they should have. At still another level, the system can include information that narrows the time window of when the patient should have taken the pill. Such information might be required where timing is critical to the efficacy of the drug or otherwise is deemed important information to obtain.

The analysis capability module 170 of the compliance monitoring system software 155 compares the data entered by the patient 120 and the date and time stamp to the data provided to the database 160 by the manufacturer as well as the date and time the patient 120 was instructed to take the pill. Again, in referring to the use of date and time for when the patient must take the pill, these terms should be understood to be applied in a sense that is commensurate with the need for precision of the time. Thus, date and time could refer to anytime during the 24 hour period following midnight. Alternatively, the date and time could be more specific and refer to 8:00 am each day. Alternatively, there could be no consideration given to the time of entry of the data and only the date on which the data is entered is considered. In sum, date and time may be as precise as needed for the drug, clinical study, interest by the health care provider, etc.

The analysis results can then be used to determine whether or not the patient was compliant with the drug dosing regimen. For example, the analysis capability module 170 could periodically analyze the data to determine the percentage of times the patient 120 correctly entered the pill ID of the pill the dispensing entity indicated it had dispensed to the patient 120. This information may be useful in validating the system to show whether or not the patients can enter the known data correctly. If the patients cannot even enter the known data correctly, the healthcare provider would have an indication that patient education is needed.

If the patient 120 entered the pill ID correctly, the analysis capability module 170 would determine the percentage of times the patient selected the distinguishable characteristic or flavor of the pill correctly. The analysis capability module 170 could also determine the percentage of times the date and time stamp associated with the data submitted by the patient 120 matches, or is within an acceptable range for the time the pill should have been taken based on the data provided to the compliance monitoring system. This may be important for effectiveness when a pill must be taken, for example, thrice daily with a particular interval between dosings. If the analysis capability module 170 determines that the patient is taking the second pill too long after the first and two close to the second, the healthcare provider would have an indication that patient education is needed to convey the importance of the dosing schedule.

The compliance monitoring system software 155 can use the results provided by the analysis capability module 170 of the software 155 to populate reports. The reporting capability module 180 of the software 155 could distribute the results reports to a variety of interested entities, including, for example, the public health program that is trying to treat a specific disease or condition; the physician, health clinic, nurse or field health worker that dispensed the pill to the patient 120, the CRO that is tracking the results of a clinical drug study. The reports might be distributed in a number of ways: they may be distributed electronically by email or by adding to an information system that tracks the patient; the reports may be posted to a web-based system that report reviewers could log into; the reports could be printed and sent using the postal service.

The reports can be varied depending upon the recipient. At one level the report is prepared to contain data on only one patient and the report would be suitable to give to that patient and/or the patient's physician. The patient could review the report to understand how they are doing on their dosing schedule. At a second level, the report is prepared for a healthcare provider or clinic and contains data on all the patients at the clinic who are on a particular drug or are part of a study in which compliance monitoring is required. The healthcare provider or clinic could use the report for a variety of purposes, including targeting patients need direct observation treatment, which patients need less oversight, whether there is a systemic problem in the compliance monitoring at that clinic that must be addressed, etc. At a third level, the report is prepared for a NGO or manufacturer who wants to know how well a program is working. It should be evident that because the data is contained within a database, an almost infinite variety of reports can be prepared depending upon the need. Creating such individual and/or global reports is well within the skill of any database programmer.

The compliance monitoring system 100 could use the analysis results in a number of different ways. The system 100 might use the results to update the patient record. For example, the analysis might automatically update the electronic patient record in a physician EMR or clinical drug study patient-tracking application. In addition, the compliance monitoring system software 155 may use the results of the analysis capability module 170 to provide recommendations for further action to undertake with regards to the patient based on levels of compliance. For example, highly compliant behavior might be indicated by the patient, after several doses, always entering the patient ID, pill ID and distinguishing flavor correctly because it matches the data in the database 160 of the software 155, and, optionally, the date and time stamp associated with the patient-entered data being a time that falls in the acceptable range for taking the pill. Highly compliant patients may not require monitoring, so the compliance monitoring system might, for example, recommend that the patient no longer receive close monitoring and be monitored at a level that requires less resources. For example, rather than require direct observational treatment, the patient may be sent email or SMS reminders to take the medicine.

Partial compliance might be indicated by a patient incorrectly entering the distinguishing flavor on one out of several doses or not using the data entry means to enter the data at all for a single dose out of several doses. Partially compliant patients may then have automated reminders (e.g., email or SMS) sent to them or phone calls made to them to remind them to take the drug dosage at the time specified by the dosing regimen. Poor compliance may be indicated by rarely entering the pill ID and/or distinguishing flavor correctly or rarely using the data entry means. In such cases, the system might recommend in-person visits to ensure the patient 120 takes the drug according to the dosing regimen. And non-compliance may be indicated when a patient never enters the data or never enters the unique pill ID or flavor data correctly. When a patient exhibits non-compliant behavior, the system might recommend in-person visits to ensure the patient takes the drug according to the drug regimen or may even indicate that the patient no longer receive the drug, or in the case of a clinical drug study, the system may recommend removing the patient from the study.

FIG. 2 is a flow chart that further illustrates the compliance monitoring system 100 by providing an example 200 of a public health program that treats patients in developing countries for tuberculosis (TB). The public health program receives the drug dosages it distributes to the patients as a donation from a pharmaceutical company. The public health program has two primary objectives: ensuring that the patients that participate in the program recover from TB by taking the drug dosages according to the drug dosing regimen and ensuring that the strain of TB does not become drug-resistant as a result of patients not adhering to the strict drug-dosing regimen.

In this hypothetical example, the pharmaceutical company produces tablets with a unique ID and distinguishing characteristic (step 210). The manufacturer creates an electronic drug dosage record that includes the drug dosage ID and distinguishing characteristic, and stores this data in an electronic database (step 220). The system also can optionally include a step of entering a patient record with unique patient IDs in the database (step 230). The patient data can be entered by a variety of entities that can correlate the provision of the individual pharmaceutical products with the individual patients, such as the healthcare provider or even the manufacturer, so long as that entity can ensure the correct patient ID and drug dosage ID are correlated (step 240). The company then directly or indirectly provides the patient with the drug dosage, such as by shipping the drug dosages to the public health program in the United States. The public health program has identified a number of facilities, health clinics, physicians and other entities it uses to dispense the drugs to individual patients. The public health program then sends a subset of the donated drugs to each of these identified entities. For example, among these entities is a health clinic in Cameroon that is the facility a specific patient with TB goes to for his healthcare needs. The clinic has requested that this patient become a recipient of the TB drugs distributed by the public health program, and the public health program has agreed.

The patient visits the health clinic and is enrolled in the program. Upon enrolling in the program, he is assigned a unique patient ID. This ID matches a record that has been created for him in the database of a compliance monitoring system. A nurse at the clinic provides him with a set of 10 pills (step 250) and instructs him to take the pills every Monday at 6 pm and to call an automated phone service that will instruct him to enter or select the following data: his patient ID, the pill ID for the pill he took orally, and the flavor of the pill after he has tasted it.

The patient returns home, and the next Monday, he takes the pill at around 6 pm (step 260). He immediately calls the automated phone service and enters the requested data (step 270). Upon hanging up the phone, the automated phone service automatically electronically submits the data the patient entered to the database of the compliance monitoring system software (step 280). Upon being added to the database, the compliance monitoring system software adds a date and time stamp that reflects the time the patient called and entered his data using the automated phone service.

Three weeks go by, and the patient continues to take his medication as instructed and continues to enter the data into the system using the automated phone service. At this point, the clinic asks the public health program to verify if the patient has been compliant with the drug dosing regimen. The public health program data analyst queries the system for information about the patient's compliance, the results of the query, or analysis, are fed to a reporting capability that generates a Patient Compliance Report for the patient in Cameroon (step 290). The system reports 100 percent compliance for the patient after three weeks (step 299). The system then uses its analysis capability to automatically produce a set of recommendations for the health clinic based on the patient's compliance level. In this case, the recommendation is to have the patient complete the 10 doses, have them come in for a check up in person, and if the compliance monitoring system determines that the patient has maintained 100 percent compliance, to give the patient a set of TB drug dosages that are not coated with a distinguishing characteristic or marked with a pill ID, and that only periodic patient visits to the clinic are required.

Figure 3:
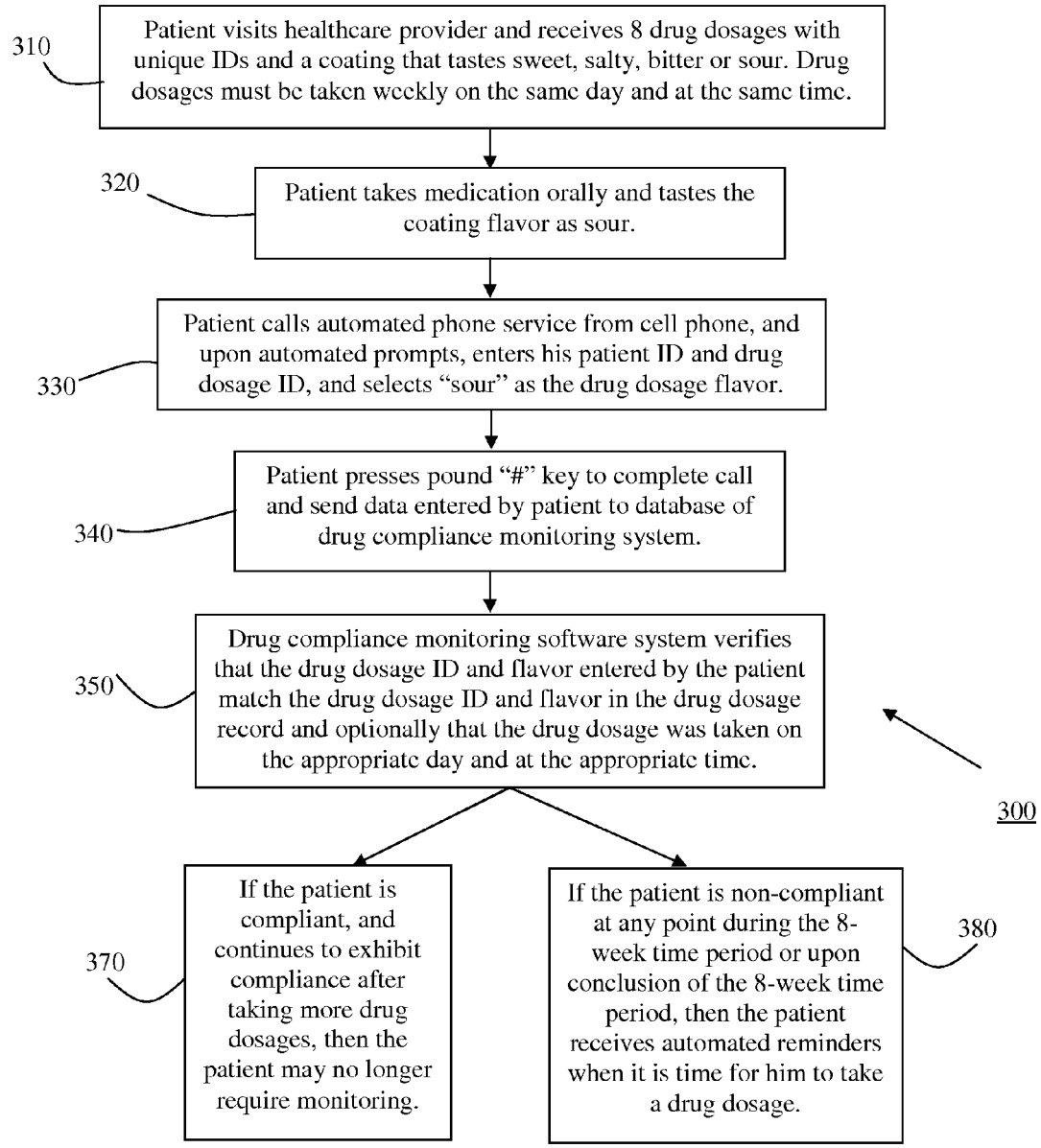
FIG. 3 is a flow chart illustrating a second implementation of a method for monitoring drug compliance.

FIG. 3 illustrates use of the compliance monitoring system 300 with a hypothetical clinical drug study in the U.S. for an HIV-AIDS drug. This hypothetical study has recruited 100 individuals with HIV-AIDS to enroll in the study. The pharmaceutical manufacturer has provided the CRO with the first set of drug dosages each patient will need for the first two weeks of the study. The drug dosages are a powder form that appears to be white until taken orally by the patient. Alternatively, the powder can include a flavor that the patient can taste upon oral administration. Each powder packet that contains an individual dosage has a unique dosage ID on its exterior that is easily readable. The unique dosage ID may be a series of numbers, letters, or combination of numbers and letters. Upon contact with the patient's tongue, the powder colors the patient's tongue with an easily distinguishable color of orange, blue, or red, or provides a flavor that the patient easily recognizes. The CRO distributes the packets containing the drugs to each patient and instructs them to take each packet daily at the same time each day for the next two weeks (step 310). The patient is also given the URL for a web site that they can log into using a username and unique patient ID the drug study has provided them. Each time they take a dosage, each patient is to go to the web site via a browser on their computer, laptop, smart phone (such as an iPhone), or other Internet connected device, log in using their username and patient ID (step 320). Once they have logged in, an online form asks them to enter the dosage ID of the individual dosage they took and then it asks them to select the color of their tongue or the flavor after they took the powder drug dosage (steps 330 and 340). Upon completion of the data entry, they are asked to click a button labeled "Submit." Clicking the Submit button transmits the data a given patient entered to the database and associates that data with their patient record that has been matched to the dosage IDs of the dosages dispensed to the patient.

After two weeks, the CRO analyzes the data to determine compliance using the analysis capability of the compliance monitoring system. A compliance report indicates that 15 of the enrollees have shown poor compliance by either not entering the data at all or by entering the data incorrectly a high percentage of the time (step 350). The compliance monitoring system recommends that these enrollees be dropped from the study or be replaced with new enrollees.

The invention can be used for numerous applications. For example, it can be used to identify patients that show low compliance with drug dosage treatments so that more effort and resources can be directed toward these low compliance patients while directing less effort and resources to those that exhibit compliant behavior (steps 370 and 380).

The results can also be used to test for compliance to determine that a given individual or population is likely to benefit from a specific drug treatment because they exhibited compliant behavior in the test. Conversely, the test for compliance may be used to identify individuals or populations on whom the drug treatment will likely be wasted unless additional resources are procured or additional measures are taken to ensure compliance.

The drug compliance monitoring system can also be used to establish a baseline of compliance before providing an intervention to improve compliance. The compliance statistics produced using the drug compliance monitoring system after establishing the baseline may then be used to determine effectiveness of the intervention over time.

The drug compliance monitoring system could also be used to automatically send electronic reminders to patient electronic devices to remind them to take their medication. Further, the system could dynamically increase or decrease the frequency of reminders based on real-time measurement of compliance. For example, as a patient's compliance level increases, the frequency of reminders decreases; conversely, as a patient's compliance level decreases, the frequency of reminders increases.

The patient data entry means can take many forms, ranging from basic to very sophisticated. In one form, the patient data entry means can be an automated phone system that the patient calls and responds to various prompts to press keypad numbers to indicate his or her response. For example, the patient may be prompted to enter his or her patient ID, the dosage form ID, and then to press a certain number to indicate the dosage form flavor, color, texture or other identifying means.

In another form, the patient data entry means may be an electronic user interface hosted on a web page that may be accessed from a browser on a cell phone or other similar handheld electronic device, a laptop, or computer.

The data may be transmitted from the patient data entry means to a server that maintains a central database. This central database contains, at a minimum, the following data: patient ID, the dosage form ID, the dosage form flavor (or other identifying means). The system may also include a second database at the clinic level or group of clinics. These databases may receive information from the central database, and may use this information to update patient records, determine compliance, measure intervention results, or to flag patients for intervention.

In another form, a clinic or group of clinics may be given views of the central database that show them current patient information, patient compliance level, intervention results, or patients flagged for intervention.

Figure 4:
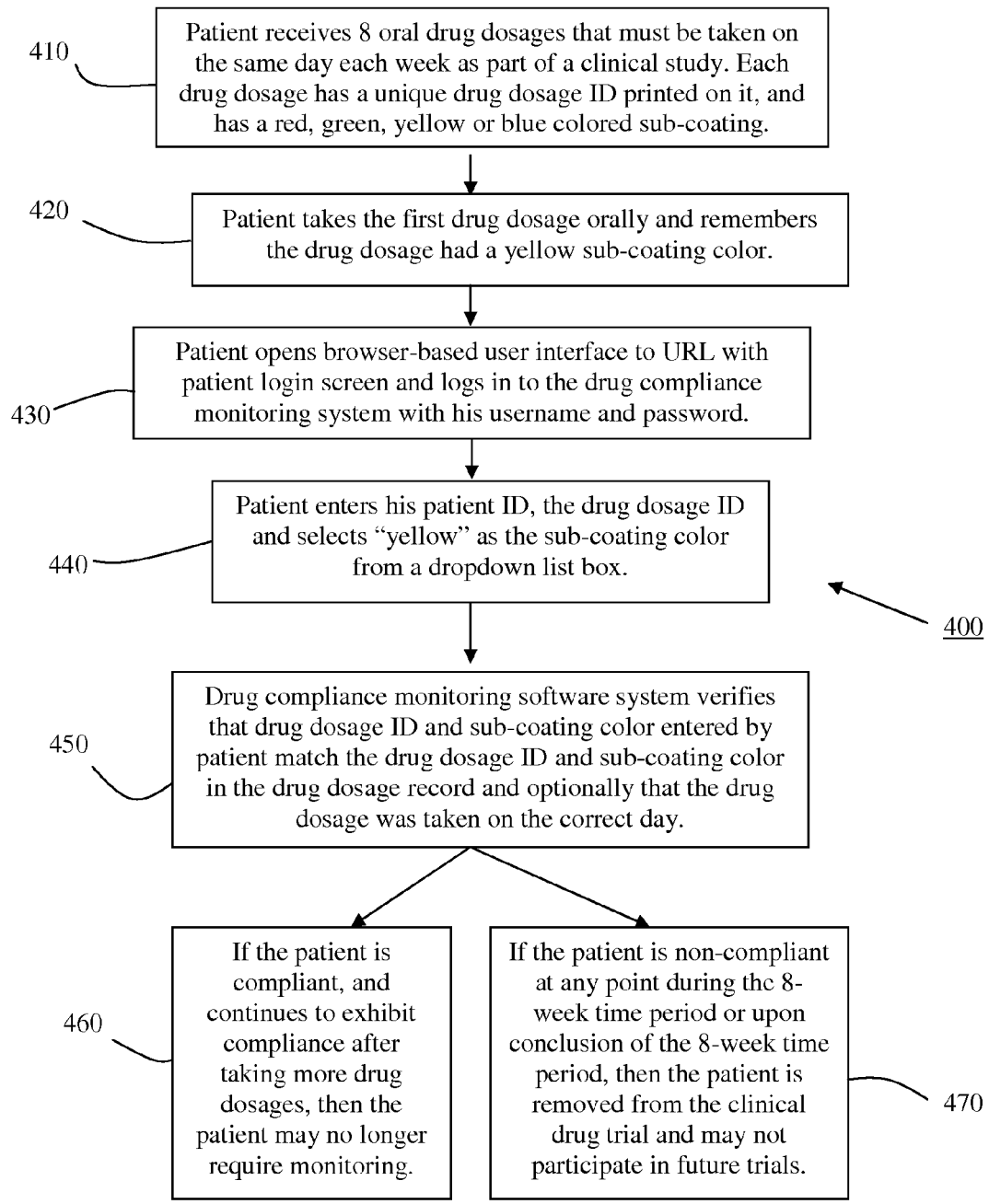
FIG. 4 is a flow chart illustrating a third implementation of a method for monitoring drug compliance.

Referring to FIG. 4, in a third implementation for a method for monitoring drug compliance the unique characteristic is the color of the dosage form. Although color may be the characteristic, flavor and/or texture may be used as the characteristic.

The invention also is applicable to addressing the problem of counterfeit drugs. In this application the dosage form or article associated with the dosage form (e.g., packaging, package insert, etc.) has an identifier/ID that is associated with a distinguishing characteristic of the drug. By using the system, an individual using the system described herein would be able to determine whether or not the dosage form is a counterfeit or not.

In the anti-counterfeiting application, the packaging can include a flavor strip that the individual can taste. The dosage form can have a unique identifier printed on it. By using the flavor and the unique identifier, the patient then can use the system to verify whether or not the unique identifier and flavor combination are correct. If they are not correct, the patient has an indication that the product is a counterfeit. To verify, the patient can repeat the process of entering the dosage form identifier and flavor into the system and verify whether or not the combination of information is correct or not. If it is not correct on the first and second usages, the individual has a strong indication that the product is a counterfeit.

This arrangement is intended to address the possibility that a counterfeiter will purchase a legitimate product and copy the information from it to make batches of products. In that event, it is expected that the counterfeiter will use the flavor and the identifiers on the dosage forms to make many batches. As such, rather than one package of the product being on the market with the unique identifier and flavor on the packaging, package insert, etc., the counterfeiter will manufacture multiple packages with this same information. Consequently, the first individual to enter this information into the system will not be alerted that the product is counterfeit. However, upon a second individual using the system to enter the same unique identifier and flavor, the entry will be flagged as indicating a possible case of counterfeiting. This can be reviewed by the manufacturer and if counterfeiting is determined, then anyone calling in with that identifier will be alerted to the counterfeit status of the product.

Figure 6:
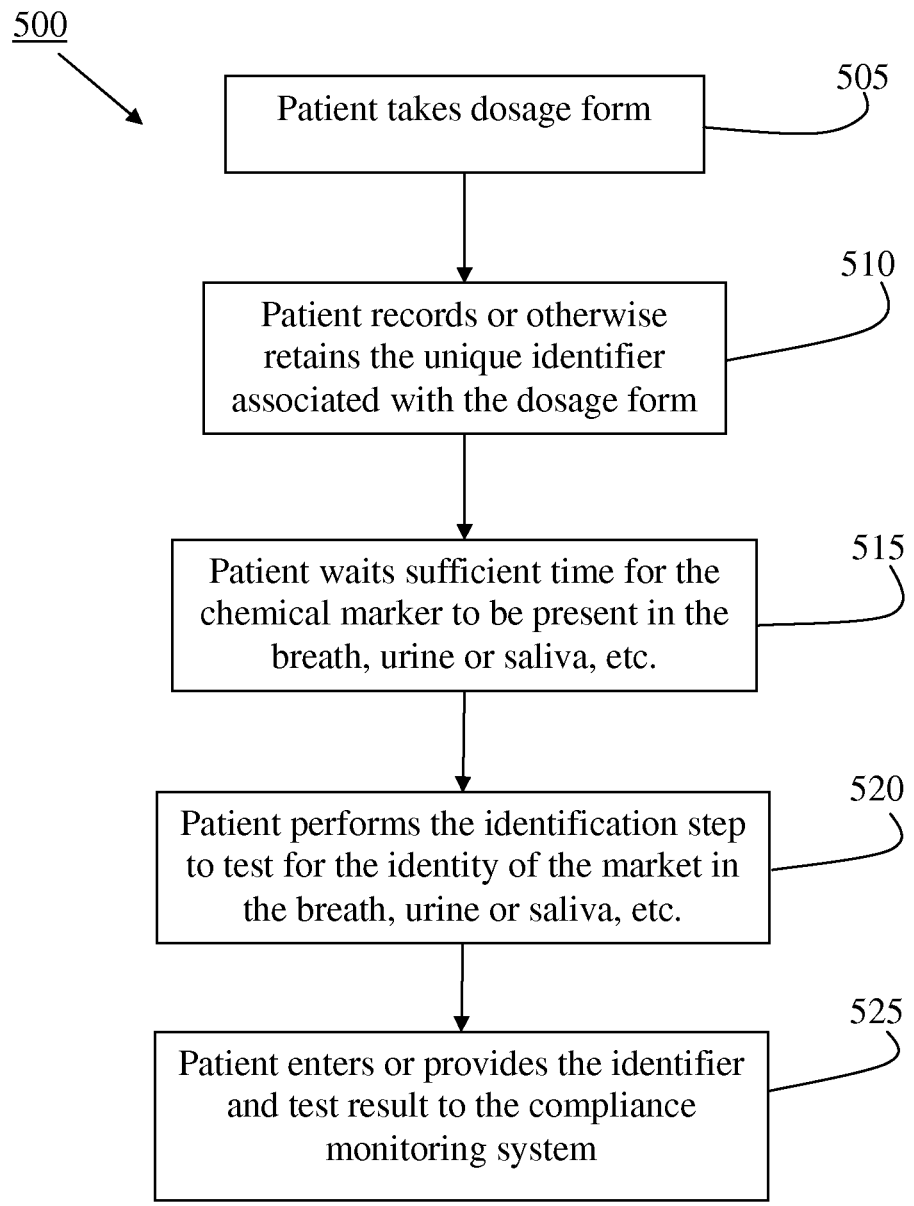
FIG. 6 is a flow chart illustrating a fourth implementation of a method of monitoring drug compliance.

Referring to FIG. 6, a fourth embodiment relates to the use of chemical markers in pharmaceutical products to determine whether or not patients are taking the pharmaceutical product. Current test methods using urine or saliva strips or breathalyzers typically measure a single compound and/or the amount of that compound present. Thus, these tests are binary—either the test is positive or negative for the presence of the single compound and the patient can see this result from the change in visual appearance of the test strip or breathalyzer output. Such a binary outcome provides a patient the ability to respond in a false manner, such as by informing the healthcare provider that the test result was positive for the compound when it was not. Although the application of these test methods in the process described in FIG. 6 relies on the same general principles as in their conventional use, the test strips and breathalyzer are configured to measure for multiple compounds. Thus, the test strip can measure compounds A, B and C, each of which can be present individually or in combination within the dosage form. Detecting the presence of one of the compounds can be a result of the chemical in the urine turning the strip a different color, e.g., red for compound A, blue for compound B and green for compound C. As a consequence, the patient will not be able to fake the response with a likelihood of success because the patient will have a 1 in 3 chance of guessing which color the strip should display when exposed to urine or saliva.

Referring again to FIG. 6, in the fourth embodiment patient compliance can be verified by a combination of the unique identifier and a characteristic of the dosage form that cannot be identified except upon administration and subsequent absorption or uptake by the body. For example, the dosage form is associated with the unique identifier but also includes a compound selected from one of three compounds that each has the characteristic of a capability of being detected after administration. Preferably, the compounds can each be detected using a noninvasive means but invasive means also may be used. For example, each of the compounds can be detected in the urine, blood, or saliva using a chemical test strip, in the breath using a breathalyzer, in the stool, tissue or hair using a reagent, etc. Considering only a measurement in the urine, after a period of time after ingestion which is sufficient to allow the compound to enter the urine, the patient uses a paper urine test strip capable of detecting and distinguishing among all three possible distinguishing compounds. Upon exposure to the patient's urine, the paper test strip clearly indicates which of the three possible distinguishing compounds has been detected or that none of the compounds has been detected if the patient did not take the pharmaceutical agent.

The compounds should be safe for human use such that the compounds can be added to a therapeutic dosage form without causing harm to patients taking the dosage form. The characteristics of such a compound may include one or more of a capability of being absorbed, lack of metabolism by the body, and not being common in the food supply. The objective is to avoid a false positive, such as when the compound is present in food commonly ingested by patients taking the dosage form. If the compound is metabolized by the body, the metabolites should be detectable and not otherwise commonly present in the body to avoid a false positive.

Examples of suitable compounds for use as chemical markers include those compounds already well-known to those of skill in the art. For example, a number of compounds are used a chemical markers in determining glomerular filtration rate (GFR). These include inulin; various radioisotope markers, including 99 mTc-labeled DTPA, 51Cr-labeled EDTA, and 125I-labeled iothalamate; and non-radioactive markers such as gadolinium, iothalamate and iohexol.

As indicated in the process set out in FIG. 6, using the dosage form in the manner according to a method 500, the patient takes the dosage form (e.g., orally, topically, inhalation, etc.) (step 505); records or otherwise retains the unique identifier associated with the dosage form (step 510); waits sufficient time for the chemical marker to be present in the breath, urine or saliva or other body-related fluid, material or tissue (step 515); performs the identification step to test for the identity of the market in the breath, urine or saliva, etc. (step 520); and provides the identifier and test result to the compliance monitoring system or health care provider (step 525). The details of this process are provided below.

In the method 500 illustrated in FIG. 6, the patient is provided with a supply of a pharmaceutical product for treating a condition or as part of a clinical drug study. The supply may be in the form of single dosages of tablets, capsules, injectable vials, topical gels or ointments, etc. Each single dosage also includes a unique identifier associated with that individual dosage. The unique identifier is easily visible to the patient. The dosage also includes the chemical marker that is part of the dosage form. For example, if the dosage form is a tablet, the tablet has been formulated to include the chemical marker within the formulation or as a coating on the dosage form. Similarly, a capsule, injectable or topical dosage form would include the chemical marker intimately mixed with the other ingredients in the dosage form. Thus, unlike the unique identifier, the chemical marker is not apparent to the patient. The chemical marker can be one compound or a combination of compounds depending on how many chemical markers are desired. It is anticipated that three chemical markers should be sufficient to prevent patients from guessing which marker is in the formulation because the patient would have a one in three chance of guessing which marker is present. To increase the odds further to one in four, some formulations can be prepared without a chemical marker. To still increase the odds further, combinations of two chemical markers can be used in a formulation such that upon using a test strip, two colors would be activated, e.g., red and green or blue and red.

In step 505, the patient takes the dosage form or is administered the dosage form. In this step the patient may simply swallow the tablet or capsule, inject the contents of a vial of the drug, or topically apply a cream, gel or ointment. The patient may take the dosage form him/herself or may have someone else administer the injectable drug.

The patient must record or retain the identifier visibly associated with the dosage form (step 510). As described above, the identifier may be a series of alpha numeric characters printed on the dosage form, dosage form container or a separate sheet associated with the dosage form such that the patient may easily know the identifier. If the identifier is present on the dosage form itself, the patient may write down the number on a piece of paper prior to administering the drug to remember it.

Because the chemical marker will be tested in a body fluid or breath, a sufficient amount of time must pass for the drug to be absorbed and be present in the fluid or breath. The drug supply is supplied with instructions setting out the amount of time the patient must wait to test the drug (step 515). This time lag between administering the drug and testing for the presence of the chemical marker will vary depending upon the route of administration of the drug and the chemical marker itself. The instructions for the product will include guidelines on long the patient must wait to conduct the test as well as how long the chemical marker is expected to be detectable. In this manner the patient will have a window in which to test for the chemical marker.

After waiting the prescribed amount of time, the patient then performs the identification step to test for the identity of the marker in the breath, urine or saliva, etc. (step 520). For example, the patient may urinate in a container and dip the test strip in the urine. In the presence of the urine, one portion of the test strip will turn or show a color which the patient will note. Similarly, the patient may place a test strip in his/her mouth and then note the color that is activated upon reaction of the chemicals in the test strip with the chemical marker in the saliva. A breathalyzer will provide a qualitative or quantitative value that is correlated with a chemical marker. Upon obtaining the result the patient notes the result.

With the result of the identification of a chemical marker, and the identifier from the dosage form, the patient next provides the identifier and test result to the compliance monitoring system or health care provider (step 525). As explained above, the patient may provide the result using a cell phone or land line, web page, etc. to enter the two pieces of data.

In one implementation, the patient might access the compliance monitoring system at the time of ingestion or administration, for example by phoning an automated voice menu number, and record the unique dosage identifier. The compliance monitoring system might then later remind the patient (e.g. by automated phone call or text message) to perform the test for the chemical marker once a sufficient period of time has elapsed. For example, the compliance monitoring system may include a database that includes pharmacokinetic data or a correlation based on pharmacokinetic data for the particular dosage form, active ingredient and/or chemical compounds or markers. Upon entering the unique dosage identifier the system may calculate access a database that contains a correlation between the dosage form, active ingredient and/or chemical compound/marker associated with that identifier to determine how long the after administration the patient must wait before detecting the presence of the chemical marker or compound in the saliva, urine, breath, etc. The automated phone call or text message may inform the patient as to the length of the window during which the patient may detect the presence of the compound or marker.

An advantage of the implementation of the fourth embodiment is the ability to prevent a patient from providing false reports without being detected by the system. This embodiment is particularly useful in that it is compatible with dosage forms using any route of administration, rather than only oral administration and provides a reliable measure of ingestion, rather than only of the placement of a dosage form in the mouth. The system also can be used to measure the chemical marker in body tissue or fluids, such as blood, tissue, stool samples, hair, skin, etc.

Figure 7:
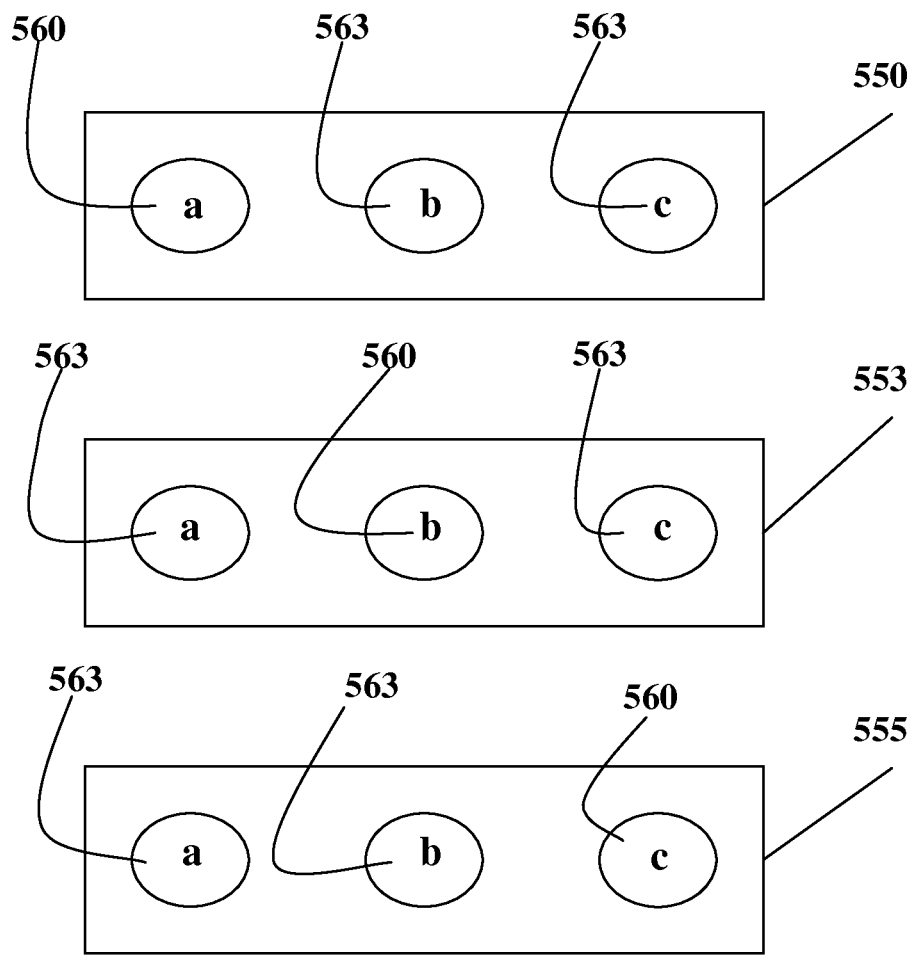
FIG. 7 is an illustration of three test strips that vary based on the region that will be activated by a marker compound or active ingredient.

In an additional implementation, a single marker compound is used in the dosage form and the test strip is modified such that one region is activated by contact with the marker compound. Referring to FIG. 7, test strips 550, 553, 555 each include a single region 560 that will be activated upon contact with the marker compound. The test strip also includes one or more additional regions 563 that will not be activated upon contact with the marker compound. The regions 560, 563 are labeled a, b and c or some other indicator that the patient can easy see and use to report which region has been activated. The region 560 includes a compound that will react with the marker compound to provide, for example, a change in color on the test strip. Such compounds are known in the art and are used, for example, in urine test strips. The regions 563 are inactive and do not contain a compound that will react with the marker compound or any other compound in the dosage form or otherwise. Thus, if the test strips 550, 553, 555 are used with a compound to be tested in urine, only region 560 will be activated by the marker compound and regions 563 will not be activated. Depending upon which test strip 550, 553, 555 is used, the position of region 560 will be varied.

The test strips are provided with the dosage form in such a manner that there is a known association between the position of region 560 and the individual dosage being administered. For example, a test strip and dosage form may be provided in a blister package that includes the unique identifier. In one implementation, the patient will open the blister package with the unique identifier printed on the packaging, call the telephone number for the compliance monitoring system, and enter the unique identifier from the packaging. The patient then will take the dosage form. After a sufficient amount of time the patient will take the test strip, urinate on it, and note which region (labeled a, b or c) is activated. The patient then will call the telephone number for the compliance monitoring system and in response to the prompts enter the region label (a, b or c) of the region 560 that has been activated. For example, if the region activated is labeled A, the patient will enter the letter A or follow instructions to press a key corresponding to the letter A.

In an alternative arrangement, after the patent contacts the compliance monitoring system for the first time and enters the unique identifier for the dosage form, the compliance monitoring system will use software, as described above, that will determine the time interval at which the marker compound can be expected to be present in the urine. Upon reaching that time interval, the compliance monitoring system will contact the patient to provide a reminder that the patient should urinate on the test strip and report the outcome to the compliance monitoring system.

Upon receiving the label for the region activated by the patient entering the label, the compliance monitoring system will take the information provided (unique dosage identifier and region label) and compare this information to that provided in a database or the like. Upon making the comparison, the compliance monitoring system will provide an output that indicates whether or not the correct region was reported as being activated for that individual dosage form.

There are numerous benefits to a compliance monitoring system that uses a single marker compound and varies regions activated on the test strip. One benefit is that the only variation in this implementation is in the test strips rather than the dosage forms. This provides for a simpler manufacturing process in which a single formulation is used for the dosage forms. Similarly, it is less expensive and much simpler to print three different configurations of test strips and merely track which of the three test strips varieties have been used with each of the particular dosage forms.

In a variation of the implementation using the test strips with multiple regions of which only a single region may be activated, the test strips may be configured to be activated by the active ingredient itself. Thus, rather than using a separate marker compound in the dosage form, the active ingredient itself is the marker compound with the test strips having one region configured to be activated by the active ingredient and one, two or more regions that are not activated by the active ingredient. For example, the test strip can be configured with two, three, or more regions of which a single region includes a compound that is activated by contact with the active ingredient. The active ingredient may be detected according to any of the methods described above, e.g., in the urine, breath, or saliva, and the region activated then reported to the compliance monitoring system. In another variation that can be applied to this embodiment or other embodiments described herein, single or multiple regions may include a compound that is activated and the regions activated can be reported, e.g., region 3 may be activated, or regions 2 and 5 may be activated, or 1, 3 and 4 may be activated. This variation increases the complexity of the test strips but also increases the likelihood that an individual cannot guess which region or regions contain the compound that is activated by the active ingredient.

The information technology portions of the systems and methods described herein may be implemented in a number of manners. For example, certain steps may be implemented in software, on a computer system and/or on the Internet. In one implementation, the system may be stored and/or run on a central server which gathers, processes, and stores information about the dosage forms. In such an implementation, the associated databases described herein may be run on the central server. Certain results may be provided on a computer display, stored in a database in computer readable memory, or printed out on paper. It is understood that most processes which can be performed mentally, on pencil and paper, or with computing means, etc. can be implemented on hardware and software. Therefore one of skill in the art would readily and easily understand that any of the methods described herein can be implemented using any software and/or hardware system. As such, in-depth and detailed description of such systems is not necessary herein. Further, prior art computer, software, Internet, and database systems are incorporated herein by reference in their entirety for their applicability to the systems described herein. Examples of arrangements of the hardware, software, data transmission, storage, etc. are shown in numerous patents and applications available by easily searching the USPTO patent and applications databases using terms such as internet and World Wide Web. Rather than include this commonly known information herein, reference is made to the general knowledge provided by searching as described above. Examples of such applications and patents are US 2007/0061393 to Moore, U.S. Pat. No. 6,546,393 to Khan, US 2007/0118399 to Avinash, and US 2008/0091466 to Butler. The understandings to data storage, transmission, processing, and display, to hardware and software used in these activities and to use of the internet, gained from these patent and applications are incorporated herein in their entirety by reference.

While several particular forms of the invention have been illustrated and described, it will be apparent that various modifications and combinations of the invention detailed in the text and drawings can be made without departing from the spirit and scope of the invention. For example, references to materials of construction, methods of construction, specific dimensions, shapes, utilities or applications are also not intended to be limiting in any manner and other materials and dimensions could be substituted and remain within the spirit and scope of the invention. Similarly, the examples of formulations described above for taste are not limited to the specific applications disclosed therein but also can be applied using the other applications of the invention, such as flavor, color, scent, etc. Accordingly, it is not intended that the invention be limited, except as by the appended claims.

What is claimed is:

1. A pharmaceutical dosage form comprising:
   an active ingredient and one or more pharmaceutically acceptable carriers, wherein at least one of the pharmaceutically acceptable carriers comprises a distinguishing characteristic assigned from a limited set of distinguishing characteristics; and
   an identifier associated with the dosage form and with the distinguishing characteristic, whereby the identifier is associated with only one distinguishing characteristic but the distinguishing characteristic may be associated with multiple identifiers,
   wherein the distinguishing characteristic is an organoleptic property determined upon oral administration of the dosage form to an individual.

2. The pharmaceutical dosage form of claim 1, wherein the organoleptic property comprises one or more of a flavor, a color, and a texture.

3. The pharmaceutical dosage form of claim 1, wherein the identifier is randomly generated.

4. The pharmaceutical dosage form of claim 1, wherein the identifier is positioned on the pharmaceutical dosage form or on an article associated with the dosage form.

5. The pharmaceutical dosage form of claim 4, wherein the article associated with the dosage form is the packaging or package insert accompanying the dosage form.

6. The pharmaceutical dosage form of claim 1, wherein the identifier is unique.

7. A pharmaceutical dosage form comprising:
   an active ingredient and one or more pharmaceutically acceptable carriers, wherein at least one of the pharmaceutically acceptable carriers comprises a distinguishing characteristic assigned from a limited set of distinguishing characteristics; and
   an identifier associated with the dosage form and with the distinguishing characteristic, whereby the identifier is associated with only one distinguishing characteristic but the distinguishing characteristic may be associated with multiple identifiers,
   wherein the distinguishing characteristic is a compound detectible in breath, bodily fluids, or tissues after ingestion, or injection or other non-oral administration of the dosage form of an individual administered the dosage form.

8. A pharmaceutical dosage form comprising:
   an active ingredient and one or more pharmaceutically acceptable carriers, wherein at least one of the pharmaceutically acceptable carriers comprises a distinguishing characteristic assigned from a limited set of distinguishing characteristics; and
   an identifier associated with the dosage form and with the distinguishing characteristic, whereby the identifier is associated with only one distinguishing characteristic but the distinguishing characteristic may be associated with multiple identifiers, wherein the distinguishing characteristic is detectible in one or more of urine, blood, saliva, breath, hair, stool or skin of an individual administered the dosage form.

9. A pharmaceutical dosage form comprising:
- an active ingredient and one or more pharmaceutically acceptable carriers, wherein at least one of the pharmaceutically acceptable carriers comprises a distinguishing characteristic assigned from a limited set of distinguishing characteristics; and
- an identifier associated with the dosage form and with the distinguishing characteristic, whereby the identifier is associated with only one distinguishing characteristic but the distinguishing characteristic may be associated with multiple identifiers,
- wherein the identifier associated with the dosage form comprises one or more alpha-numeric characters.

10. A method for monitoring compliance with a pharmaceutical dosing regimen, the method comprising:
- providing a dosage form comprising an active ingredient and one or more pharmaceutically acceptable carriers, wherein at least one of the pharmaceutically acceptable carriers has a distinguishing characteristic, and an identifier, the distinguishing characteristic being assigned from a limited set of distinguishing characteristics and being determined upon or at a time after administration of the dosage form, and the identifier being associated with the dosage form and with the distinguishing characteristic, whereby the identifier is associated with only one distinguishing characteristic but the distinguishing characteristic may be associated with multiple identifiers;
- storing the identifier and distinguishing characteristic in a look up table in a database on computer readable memory, wherein the identifier and distinguishing characteristic are stored in the database in a relationship;
- providing software stored on computer readable memory in which the software is configured to receive a patient identifier, the dosage form identifier and the distinguishing characteristic;
- upon receipt of the patient identifier, dosage form identifier and distinguishing characteristic in the software, determining if that provided dosage form identifier is associated in the database with that provided distinguishing characteristic.

11. The method of claim 10, wherein determining if that provided dosage form identifier is associated in the database with that provided distinguishing characteristic provides a measure of compliance.

12. The method of claim 10, further comprising:
- providing the identifier associated with the dosage form at the time of administering the dosage form;
- using software to determine when the distinguishing characteristic should be detected;
- sending a notification to the patient to detect the distinguishing characteristic.

13. The method of claim 10, when the notification is sent at the time that the distinguishing characteristic should be detected.

14. A method for monitoring compliance with a pharmaceutical dosing regimen, the method comprising:
- providing a dosage form comprising an active ingredient and one or more pharmaceutical acceptable carriers, wherein at least one of the pharmaceutically acceptable carriers has a distinguishing characteristic, and an identifier, the distinguishing characteristic being assigned from a limited set of distinguishing characteristics and being determined in breath, bodily fluids, or tissues after ingestion, or injection or other non-oral administration of the dosage form, and the identifier being associated with the dosage form and with the distinguishing characteristic, whereby the identifier is associated with only one distinguishing characteristic but the distinguishing characteristic may be associated with multiple identifiers;
- storing the identifier and distinguishing characteristic in a look up table in a database on computer readable memory, wherein the identifier and distinguishing characteristic are stored in the database in a relationship;
- providing software stored on computer readable memory in which the software is configured to receive a patient identifier, the dosage form identifier and the distinguishing characteristic;
- upon receipt of the patient identifier, dosage form identifier and distinguishing characteristic in the software, determining if that provided dosage form identifier is associated in the database with that provided distinguishing characteristic.

15. The method of claim 14, wherein determining if that provided dosage form identifier is associated in the database with that provided distinguishing characteristic provides a measure of compliance.

16. The method of claim 14, further comprising:
- providing the identifier associated with the dosage form at the time of administering the dosage form;
- using software to determine when the distinguishing characteristic should be detected;
- sending a notification to the patient to detect the distinguishing characteristic.

17. The method of claim 14, when the notification is sent at the time that the distinguishing characteristic should be detected.

18. A method for monitoring compliance with a pharmaceutical dosing regimen, the method comprising:
- providing a dosage form comprising an active ingredient, a compound capable of being detected, and one or more pharmaceutical acceptable carriers;
- providing a test strip to a patient, the test strip having at least two regions, wherein each region can be distinguished from another region on the test strip and at least one region includes a reagent that can be activated by the compound capable of being detected when the compound contacts the reagent;
- after administration of the dosage form to a patient, contacting the test strip with a body fluid or substance containing the compound capable of being detected; and
- reporting the region activated on the test strip or the lack of a region being activated on the test strip.

19. The method of claim 18, wherein the active ingredient is the compound capable of being detected.

* * * * *